(12) United States Patent
Cech et al.

(10) Patent No.: US 12,037,366 B2
(45) Date of Patent: Jul. 16, 2024

(54) OMPG VARIANTS

(71) Applicant: Roche Sequencing Solutions, Inc., Pleasanton, CA (US)

(72) Inventors: Cynthia Cech, Mountain View, CA (US); Tim Craig, Mountain View, CA (US); Christos Tzitzilonis, Mountain View, CA (US); Alexander Yang, Mountain View, CA (US); Liv Jensen, Mountain View, CA (US); Charlotte Yang, Mountain View, CA (US); Corissa Harris, Mountain View, CA (US); Matthew Dipietro, Gilroy, CA (US); Dhruti Dalal, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 18/449,904

(22) Filed: Aug. 15, 2023

(65) Prior Publication Data

US 2024/0010688 A1 Jan. 11, 2024

Related U.S. Application Data

(63) Continuation of application No. 16/925,848, filed on Jul. 10, 2020, now Pat. No. 11,767,348, which is a continuation of application No. 15/762,092, filed as application No. PCT/EP2016/072224 on Sep. 20, 2016, now Pat. No. 10,752,658.

(60) Provisional application No. 62/333,672, filed on May 9, 2016, provisional application No. 62/222,197, filed on Sep. 22, 2015.

(51) Int. Cl.
*C12Q 1/68* (2018.01)
*A61K 39/02* (2006.01)
*C07K 14/245* (2006.01)
*C12N 9/12* (2006.01)
*C12Q 1/6874* (2018.01)
*G01N 33/68* (2006.01)

(52) U.S. Cl.
CPC .......... *C07K 14/245* (2013.01); *C12N 9/1252* (2013.01); *C12Q 1/68* (2013.01); *C12Q 1/6874* (2013.01); *C12Y 207/07007* (2013.01); *G01N 33/6803* (2013.01); *C07K 2319/00* (2013.01)

(58) Field of Classification Search
None
See application file for complete search history.

(56) References Cited

U.S. PATENT DOCUMENTS 10,752,658 B2 * 8/2020 Cech .................. G01N 33/6803
11,767,348 B2 * 9/2023 Cech .................. C12Q 1/6874
435/6.11

OTHER PUBLICATIONS

Korkmaz-Ozkan et al (J. Molec. Biol. 401(1): 56-67. Aug. 2010).*
Chen et al (PNAS, 105(17): 6272-6277, Apr. 2008).*
Grosse et al (Biochem. 2014, 53: 4826-4838).*
Database Accession # XP055320050. Aug. 2014.*

* cited by examiner

*Primary Examiner* — Jennifer E Graser
(74) *Attorney, Agent, or Firm* — FishBroyles, LLP; Jason M. Pass

(57) ABSTRACT

The present disclosure provides variant OmpG polypeptides, compositions comprising the OmpG variant polypeptides, and methods for using the variant OmpG polypeptides as nanopores for determining the sequence of single stranded nucleic acids. The variant OmpG nanopores reduce the ionic current noise versus the parental OmpG polypeptide from which they are derived and thereby enable sequencing of polynucleotides with single nucleotide resolution. The reduced ionic current noise also provides for the use of these OmpG nanopore variants in other single molecule sensing applications, e.g., protein sequencing.

20 Claims, 22 Drawing Sheets

Specification includes a Sequence Listing.

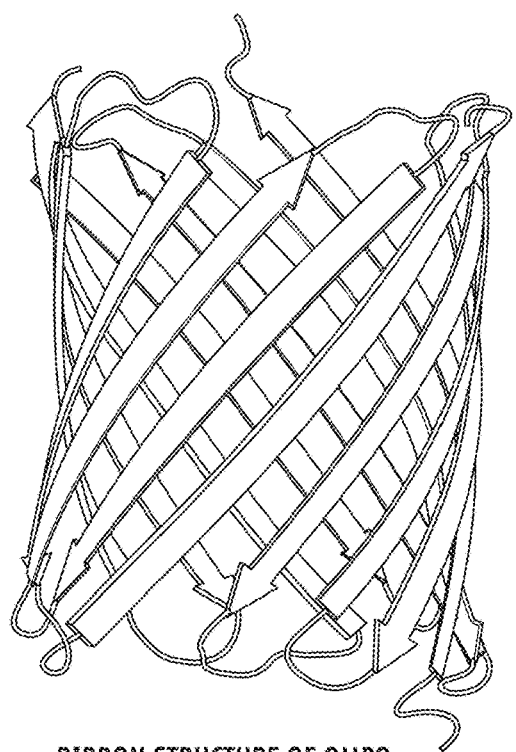
RIBBON STRUCTURE OF OMPG    FIG. 1A
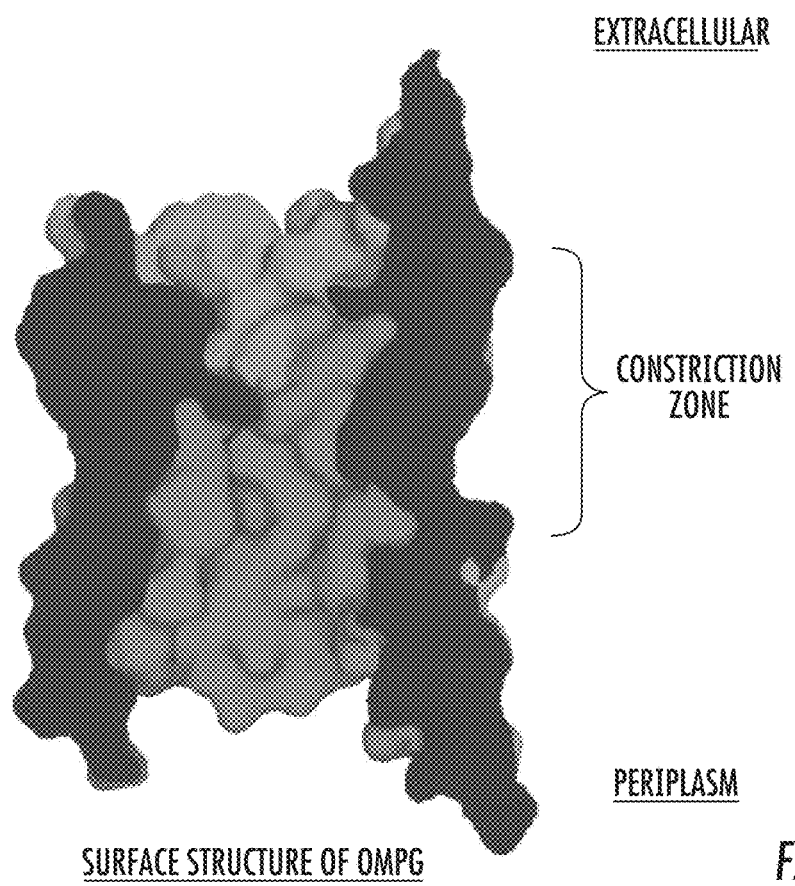
EXTRACELLULAR
CONSTRICTION ZONE
PERIPLASM
SURFACE STRUCTURE OF OMPG    FIG. 1B

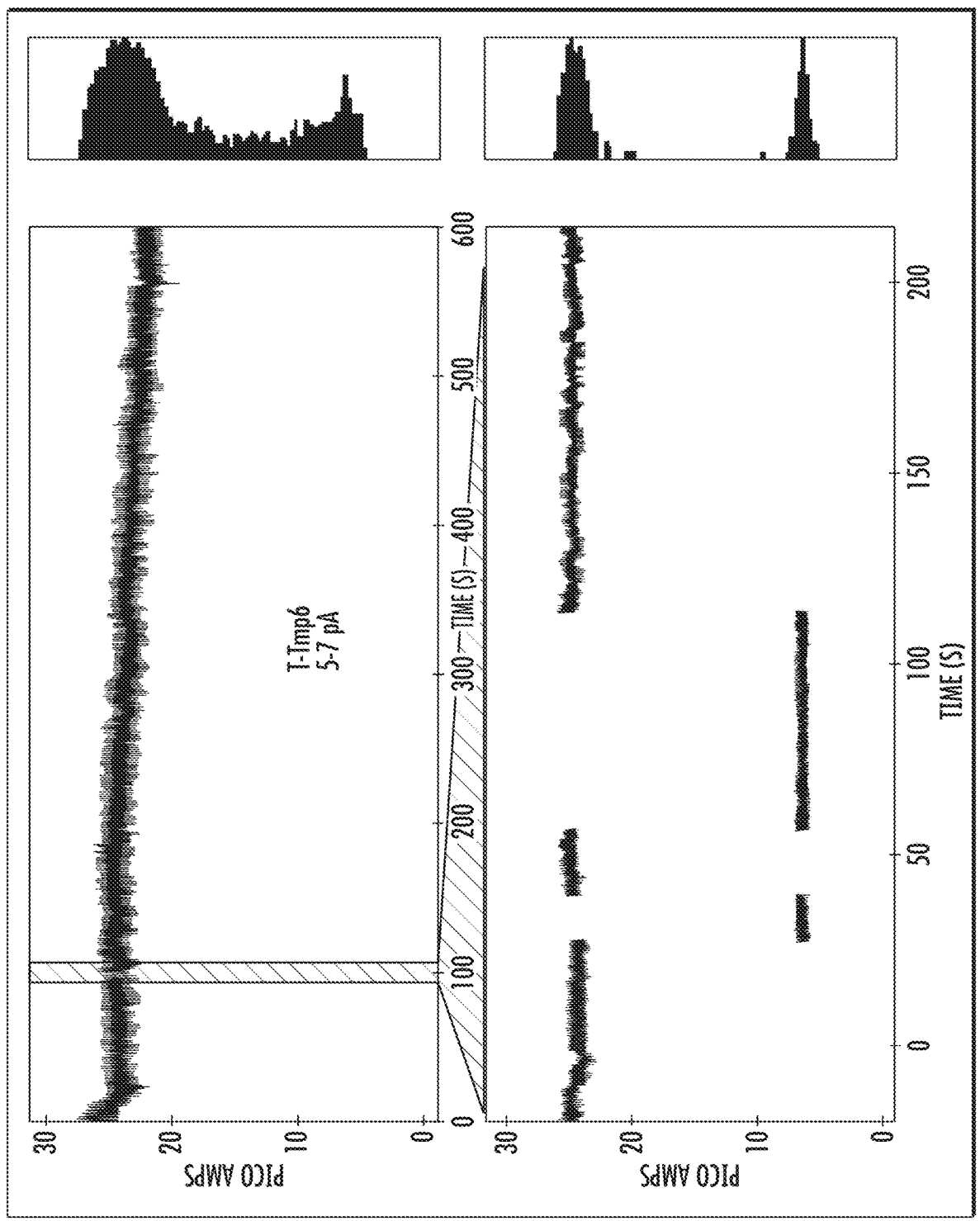

FIG. 9E

OMPG VARIANTS

CROSS REFERENCE TO RELATED APPLICATIONS

The present application is a continuation of U.S. application Ser. No. 16/925,848, filed Jul. 10, 2020, which is a continuation of U.S. application Ser. No. 15/762,092, filed Mar. 21, 2018 which claims priority to application filed under 35 U.S.C. § 371 as the U.S. national phase of International Patent Application No. PCT/EP2016/072224, filed Sep. 20, 2016, which designated the United States and claims priority to U.S. Provisional Application No. 62/333,672, filed May 9, 2016, and to U.S. Provisional Application No. 62/222,197, filed Sep. 22, 2015, each of which is hereby incorporated in its entirety including all tables, figures and claims.

SEQUENCE LISTING

The application contains a Sequence Listing which has been submitted electronically in .XML format and is hereby incorporated by reference in its entirety. Said .XML copy, created on Aug. 14, 2023, is named "04338.524US3.xml" and is 32,619 bytes in size. The sequence listing contained in this .XML file is part of the specification and is hereby incorporated by reference herein in its entirety.

TECHNICAL FIELD

Engineered variants of monomeric nanopores are provided for use in determining the sequence of nucleic acids and proteins.

BACKGROUND

Protein nanopores have become powerful single-molecule analytical tools that enable the study of fundamental problems in chemistry and biology. In particular, nanopores have attracted considerable attention because of their potential applications in the detection and analysis of single biomolecules, such as DNA, RNA, and proteins.

Molecular detection using a single nanopore is achieved by observing modulations in ionic current flowing through, or the voltage across the pore during an applied potential. Typically, a nanopore that spans an impermeable membrane is placed between two chambers that contain an electrolyte, and voltage is applied across the membrane using electrodes. These conditions lead to ionic flux through the pore. Nucleic acid or protein molecules can be driven through the pore, and structural features of the biomolecules are observed as measurable changes in the trans-membrane current or voltage.

A challenge of nanopore sequencing is resolving nucleotide sequences at a single base level. One of the factors that hinders the discrimination of individual nucleotide bases is the fluctuation in the ionic current flow through the nanopore that is inherent to the structure of the nanopore.

SUMMARY OF THE INVENTION

The present disclosure provides variant outer membrane protein G (OmpG) polypeptides, compositions comprising the OmpG variant polypeptides, and methods for using the variant OmpG polypeptides as nanopores for nucleic acid (e.g., DNA, RNA) and/or polymeric (e.g., protein) sequencing and counting. The variant OmpG nanopores reduce the ionic current noise of the parental OmpG polypeptide from which they are derived.

In one aspect, the disclosure provides variant OmpG polypeptides. In one embodiment, provided is an isolated variant of a parental OmpG of SEQ ID NO:2 or homolog thereof, wherein the variant comprises a deletion of one or more of amino acids 216-227, amino acid substitution E229A, and a mutation of one or more of amino acids R211, E15, R68, Y50, E152, E174, E17, D215, Y259, K114, E174, F66, and E31, and wherein said variant retains the ability to form a nanopore. In some embodiments, the OmpG variant has at least 70% identity to the OmpG of SEQ ID NO:2. In other embodiments, the variant OmpG comprises the linker-His-SpyTag construct of SEQ ID NO:16.

In another embodiment, provided is an isolated variant of a parental OmpG of SEQ ID NO:2 or homolog thereof, wherein the variant comprises a deletion of one or more of amino acids 216-227, amino acid substitution E229A, and a deletion of amino acid D215, and retains the ability to form a pore. The isolated variant can further comprise a mutation of one or more of amino acids R211, E15, R68, Y50, E152, E174, E17, D215, Y259, K114, E174, F66, and E31 of SEQ ID NO:2. In some embodiments, the OmpG variant has at least 70% identity to the OmpG of SEQ ID NO:2. In other embodiments, the variant OmpG comprises the linker-His-SpyTag construct of SEQ ID NO:16.

In some embodiments the isolated OmpG variant comprises a deletion of one or more of amino acids 216-227 and a substitution Y50K. In other embodiments, the OmpG variant further comprises a deletion of D215.

In another embodiment, the isolated OmpG variant comprises a "circular permutation" in which one or more C-terminal β-strand(s) of the parental OmpG are moved to the N-terminus of the protein sequence. In one embodiment, the C-terminal β-strand is moved to the N-terminus, retaining the penultimate β-strand of the parental OmpG as the new C-terminus of the protein. In other embodiments, two or more β-strands are moved to the N-terminus. Optionally, the variant includes a tag sequence (e.g., comprising a "SpyTag" or "His-SpyTag: sequence, optionally further comprising one or more linker sequences (e.g., SEQ ID NO:16) at the C-terminus, downstream from the penultimate β-strand of the parental OmpG. Optionally, the variant includes a linker sequence, e.g., GSG, between the new N-terminal β-strand that was moved from the C-terminus of the parental OmpG and the β-strand that was previously at the N-terminus of the parental OmpG. In one embodiment, the variant is a variant of the E. coli OmpG depicted in SEQ ID NO:2, or a homolog thereof. In one embodiment, the variant comprises movement of amino acid residues 267-280 of SEQ ID NO:2 from the C-terminus to the N-terminus of SEQ ID NO:2, optionally with a linker, e.g., GSG, between previous residue 280 and the N-terminus of SEQ ID NO:2, and optionally with a methionine (M) residue at the N-terminus of the variant, prior to previous residue 267, and optionally with the amino acid sequence depicted in SEQ ID NO:16 at the C-terminus of the variant. In one embodiment, the variant has the amino acid sequence depicted in SEQ ID NO: 17.

In some embodiments, the variant OmpG retains the ability to form a nanopore in a lipid or polymer layer. In other embodiments, the OmpG variant displays a reduced ionic current noise when an applied voltage is applied across the lipid bilayer. In other embodiments, the variant OmpG has reduced ionic current noise as compared to the parental E. Coli OmpG having the amino acid sequence of SEQ ID NO:2. Additionally, the variant OmpG can further comprise a genetic polymerase fusion, e.g., the isolated OmpG variant comprises a polymerase that is operably linked to said variant OmpG (still functional after linkage).

In yet other embodiments, the variant OmpG enables detection of the incorporation of nucleotides by said polymerase into a growing nucleic acid strand with single nucleotide resolution.

In another aspect, the disclosure provides isolated nucleic acids that encode the variant OmpG polypeptides. In one embodiment, provided is an isolated nucleic acid comprising a polynucleotide sequence encoding a variant of the parental OmpG of SEQ ID NO:2, wherein said variant OmpG comprises a deletion of one or more of amino acids 216-227, amino acid substitution E229A, and (i) a deletion of amino acid D215; and/or (ii) a mutation of one or more of amino acids R211, E15, R68, Y50, E152, E174, E17, D215, Y259, K114, E174, F66, and E31. In other embodiments, the polynucleotide sequence encodes a variant having at least 70% identity to the OmpG of SEQ ID NO:2. In other embodiments, the polynucleotide sequence encodes an OmpG circular permutation variant, e.g., a circular permutation variant of SEQ ID NO:2 or a homolog thereof, as described above, e.g., SEQ ID NO:17.

In another aspect, provided is an expression vector that comprises an isolated nucleic acid that encodes a variant OmpG polypeptide as disclosed herein. In one embodiment, the expression vector comprises a nucleic acid comprising a polynucleotide sequence encoding a variant of the parental OmpG of SEQ ID NO:2, wherein said variant OmpG comprises a deletion of one or more of amino acids 216-227, amino acid substitution E229A, and (i) a deletion of amino acid D215, i.e., del215; and/or (ii) a mutation of one or more of amino acids R211, E15, R68, Y50, E152, E174, E17, D215, Y259, K114, E174, F66, and E31. In another embodiment the expression vector comprises a nucleic acid encoding a polynucleotide sequence that encodes an OmpG circular permutation variant, e.g., a circular permutation variant of SEQ ID NO:2 or a homolog thereof, as described above, e.g., SEQ ID NO:17.

In another aspect, provided is a host microorganism that comprises an expression vector that expresses an OmpG variant described herein. In one embodiment, the host microorganism comprises an expression vector comprising a polynucleotide sequence encoding a variant of the parental OmpG of SEQ ID NO:2, wherein said variant OmpG comprises a deletion of one or more of amino acids 216-227, amino acid substitution E229A, and (i) a deletion of amino acid D215; and/or (ii) a mutation of one or more of amino acids R211, E15, R68, Y50, E152, E174, E17, D215, Y259, K114, E174, F66, and E31. In another embodiment, the host microorganism comprises an expression vector comprising a polynucleotide sequence encoding an OmpG circular permutation variant, e.g., a circular permutation variant of SEQ ID NO:2 or a homolog thereof, as described above, e.g., SEQ ID NO:17.

In another aspect, a method for producing a variant OmpG in a host cell is provided. In one embodiment, the method comprises a) transforming a host cell with an expression vector comprising a nucleic acid encoding a variant of the parental OmpG of SEQ ID NO:2, wherein said variant OmpG comprises a deletion of one or more of amino acids 216-227, amino acid substitution E229A, and (i) a deletion of amino acid D215; and/or (ii) a mutation of one or more of amino acids R211, E15, R68, Y50, E152, E174, E17, D215, Y259, K114, E174, F66, and E31; and b) culturing the host cell under conditions suitable for the production of the variant OmpG. In another embodiment, the method comprises a) transforming a host cell with an expression vector comprising a polynucleotide sequence that encodes an OmpG circular permutation variant, e.g., a circular permutation variant of SEQ ID NO:2 or a homolog thereof, as described above, e.g., SEQ ID NO:17; and b) culturing the host cell under conditions suitable for the production of the variant OmpG. In other embodiments, the method further comprises recovering the produced variant.

In another aspect, a method is provided for sequencing a nucleic acid sample with the aid of a variant OmpG nanopore. In one embodiment, the method comprises: (a) providing tagged nucleotides into a reaction chamber comprising the variant OmpG nanopore, wherein an individual tagged nucleotide of the tagged nucleotides contains a tag coupled to a nucleotide, which tag is detectable with the aid of said nanopore; (b) carrying out a polymerization reaction with the aid of a single polymerase coupled to said variant OmpG nanopore, thereby incorporating an individual tagged nucleotide of the tagged nucleotides into a growing strand complementary to a single stranded nucleic acid molecule from the nucleic acid sample; and (c) detecting, with the aid of the variant OmpG nanopore, a tag associated with the individual tagged nucleotide during incorporation of the individual tagged nucleotide, wherein the tag is detected with the aid of the variant OmpG nanopore while the nucleotide is associated with the polymerase.

In another aspect, provided is a chip for sequencing a nucleic acid sample. In one embodiment, the chip comprises a plurality of the variant OmpG nanopores disclosed herein, an OmpG nanopore of the plurality being disposed adjacent or in proximity to an electrode, wherein said nanopore is individually addressable and has a single polymerase attached to the nanopore; and wherein an individual nanopore detects the tag associated with the tagged nucleotide during incorporation of the nucleotide into a growing nucleic acid chain by the polymerase.

In another aspect, a composition is provided. In one embodiment, the composition comprises a plurality of polymerase enzymes, each complexed with a template nucleic acid, each polymerase enzyme attached to a variant OmpG nanopore as disclosed herein or attached proximal to the variant OmpG nanopore, and nucleic acid sequencing reagents including at least one tagged nucleotide or nucleotide analog.

BRIEF DESCRIPTION OF THE DRAWINGS

FIGS. 1A and 1B depict the architecture of the wild-type OmpG pore from *E. coli* as a ribbon structure (FIG. 1A) and as a surface representation (FIG. 1B). The constriction zone of the OmpG nanopore is shown.

(FIG. 4A)), R68N (SEQ ID NO:7; (FIG. 4B)), R211N (SEQ ID NO:8; (FIG. 4C)), E17K (SEQ ID NO:9: (FIG. 4D)), and the amino acid deletion del215 (SEQ ID NO:10; (FIG. 4E)).

FIGS. 7A-7D depict the identification of each of the tagged nucleotides detected in FIG. 6 by the variant OmpG nanopore ΔL6/E229A-del215 (SEQ ID NO:10) as separate changes in baseline open channel current for each of the four tagged nucleotides. Measurements were made with the application of a direct current (DC).

FIGS. 9A-9E depicts a protein alignment of bacterial membrane protein homologs of the OmpG from *E. coli* (SEQ ID NOS 1 and 12-15, respectively, in order of appearance).

DETAILED DESCRIPTION

Figure 2:
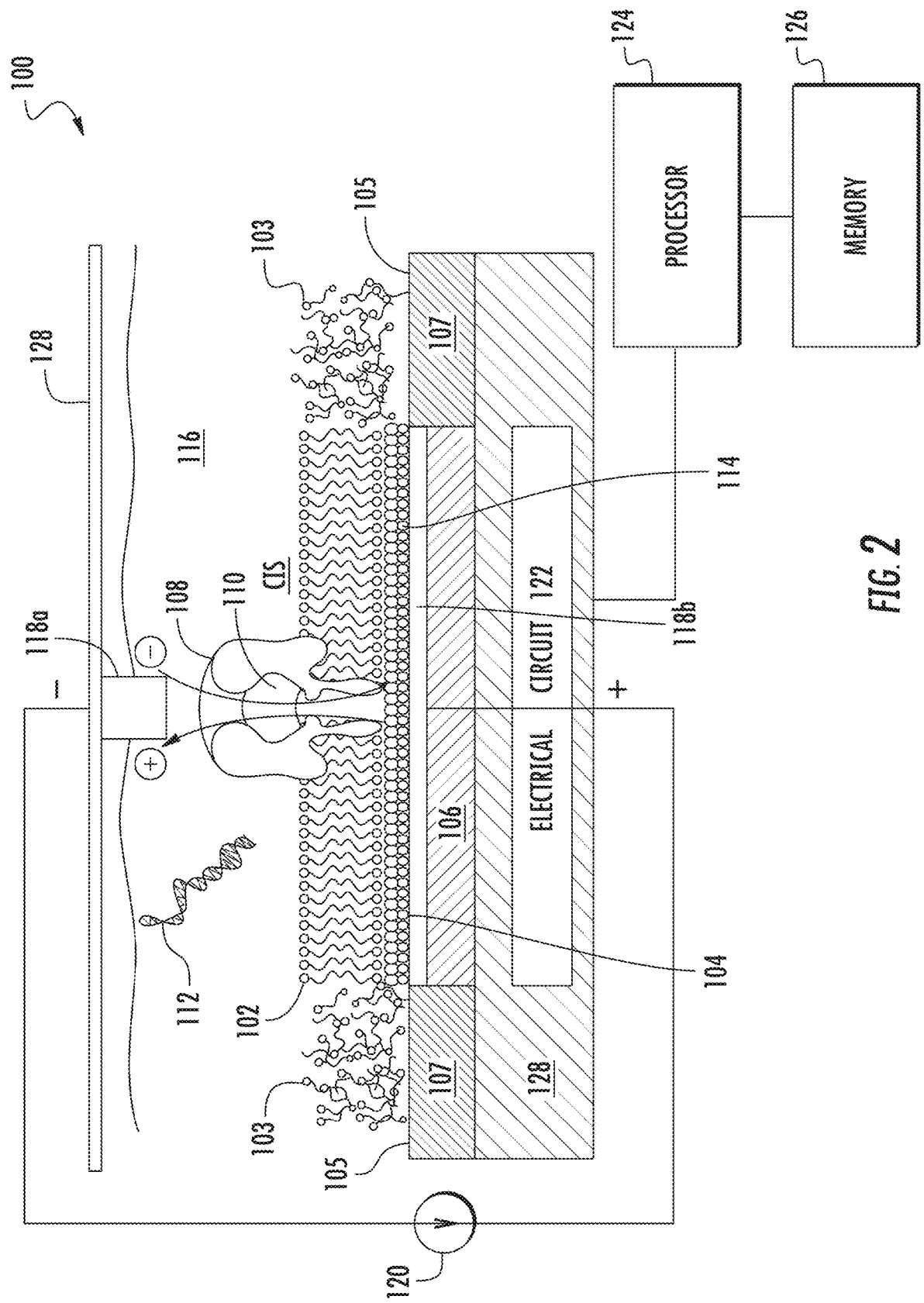
FIG. 2 is a schematic diagram of an embodiment of a circuit used in a nanopore device for controlling an electrical stimulus and for detecting electrical signatures of an analyte molecule.

A detailed description of one or more embodiments of the invention is provided below along with accompanying figures that illustrate the principles of the invention. The invention is described in connection with such embodiments, but the invention is not limited to any embodiment. The scope of the invention is limited only by the claims, and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The outer membrane (OM) of Gram-negative bacteria contains a large number of channel proteins that mediate the uptake of ions and nutrients necessary for growth and functioning of the cell. In contrast with other multimeric proteinaceous nanopores such as α-hemolysin and ClyA, outer membrane protein G (OmpG) from *Escherichia coli* (*E. coli*) functions as a monomer. The crystal structure of *E. coli* K12 OmpG has been determined (Subbarao and van den Berg, *J Mol Biol*, 360:750-759 [2006]). The structure shows that the OmpG barrel consists of 14 β-strands connected by seven flexible loops on the extracellular side and seven short turns on the periplasmic side (FIG. 1A). The OmpG channel has its largest diameter (20-22 Å) at the periplasmic exit and tapers to a constriction located close to the extracellular side (FIG. 1B). The constriction is formed by the side chains of inward pointing residues of the barrel wall, and not by surface loops folding inwards. This architecture gives rise to a relatively large central pore with a circular shape and a diameter of about 13 Å.

When current is measured across a wild-type OmpG nanopore, the nanopore spontaneously transitions between open and closed states during an applied potential, which gives rise to flickering single channel currents. The longest of the extracellular loop of OmpG, loop 6, has been recognized as the main gating loop that closes the pore at low pH and opens it at high pH.

The present disclosure provides variant OmpG polypeptides, compositions comprising the variant OmpG polypeptides, and methods for using the variant OmpG polypeptides as nanopores for determining the sequence of single stranded nucleic acids. The variant OmpG nanopores reduce the ionic current noise of the parental OmpG polypeptide from which they are derived and thereby enable sequencing of polynucleotides with single nucleotide resolution. The reduced ionic current noise also provides for the use of these OmpG nanopore variants in other single molecule sensing applications, e.g., protein sequencing.

Definitions

The term "variant" herein refers to an OmpG derived from another (i.e., parental) OmpG and contains one or more amino acid mutations (e.g., amino acid deletion, insertion or substitution) as compared to the parental OmpG.

The term "isolated" herein refers to a molecule, e.g., a nucleic acid molecule, that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The term "mutation" herein refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

The term "wild-type" herein refers to a gene or gene product, which has the characteristics of that gene or gene product when isolated from a naturally-occurring source.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

The terms "polynucleotide" and "nucleic acid" are herein used interchangeably to refer to a polymeric molecule composed of nucleotide monomers covalently bonded in a chain. DNA (deoxyribonucleic acid) and RNA (ribonucleic acid) are examples of polynucleotides.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature. A tag may block the flow of current through a nanopore.

The term "nanopore" herein refers to a pore, channel or passage formed or otherwise provided in a membrane. A membrane may be an organic membrane, such as a lipid bilayer, or a synthetic membrane, such as a membrane formed of a polymeric material. The nanopore may be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nm to about 1000 nm. Some nanopores are proteins. OmpG is an example of a protein nanopore.

The term "spontaneous gating" refers to changes in ion current related to the channel's inherent structural changes. For example, OmpG in planar lipid bilayers undergoes pH-dependent rapid fluctuations between open and closed states of the pore, which manifest themselves as intense "flickering" in current recordings and contributes to the overall noise of the channel.

The terms "noise" and "ionic current noise" are herein used interchangeably and refer to the random fluctuations of electrical signal, which include current fluctuations contributed by spontaneous gating and current fluctuations contributed by the inherent architecture of the nanopore barrel. For example, the tertiary make-up of the nanopore barrel can comprise more than one recognition site for the analyte that is being sensed by the nanopore thereby inducing additional signals that contribute to the overall noise of the channel.

The term "upward noise" herein refers to fluctuations of ionic current to levels greater than mean open channel current.

The term "downward noise" herein refers to fluctuations of ionic current to levels lower than mean open channel current.

The term "positive current" herein refers to a current in which a positive charge, e.g., $K^+$, moves through the pore from the trans to the cis side, or negative charge, e.g., $Cl^-$, moves from the cis to the trans side. For example, with reference to FIG. 2, cis corresponds to 106 and trans corresponds to 116.

The term "constriction amino acids" herein refers to the amino acids that determine the size of the OmpG pore at the constriction zone. The constriction zone may be the same as the constriction zone of the wild-type OmpG or it may be a constriction zone introduced via protein engineering, or by the introduction of a molecular adapter.

The term "parental" or "parent" herein refers to an OmpG to which modifications, e.g., substitution(s), insertion(s), deletion(s), and/or truncation(s), are made to produce the OmpG variants disclosed herein. This term also refers to the polypeptide with which a variant is compared and aligned. The parent may be a naturally occurring (wild type) polypeptide, or it may be a variant thereof, prepared by any suitable means. In preferred embodiments, "parental" proteins are homologs of one another.

The terms "purified" herein refers to a polypeptide, e.g., a variant OmpG polypeptide, that is present in a sample at a concentration of at least 95% by weight, or at least 98% by weight of the sample in which it is contained.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al., *Organic Letters*, 8:5345-5347

Also encompassed are nucleoside tetraphosphate, nucleoside pentaphosphates and nucleoside hexaphosphates.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature, which signature may be detected with the aid of a nanopore (US2014/013616). A tag can also be attached to a polyphosphate as is shown in FIG. 13 of US2014/013616.

Variant OmpG Polypeptides

In one aspect, the disclosure provides variant OmpG polypeptides. The variant OmpG polypeptides can be derived from a parental OmpG of *E. coli*, for example, the parental OmpG depicted in SEQ ID NO:2. A parental OmpG can be a homolog of the parental OmpG from *E. coli*.

Although *E. coli* sp. strain K12 OmpG (SEQ ID NO: 2) is used as a starting point for discussing variant OmpGs herein, it will be appreciated that other gram-negative bacterial OmpGs having a high degree of homology to the *E. coli* sp. strain K12 OmpG may serve as a parental OmpG within the scope of the compositions and methods disclosed herein. This is particularly true of other naturally-occurring bacterial OmpGs that include only minor sequence differences in comparison to *E. coli* sp. strain K12 OmpG, not including the substitutions, deletions, and/or insertions that are the subject of the present disclosure. For example, OmpG homologs expressed in *Salmonella* sp., *Shigella* sp., and *Pseudomonas* sp. can be used as parental OmpG polypeptides from which variant forms can be derived. In some embodiments, the nanopore is a pore from a mitochondrial membrane.

Homologs of the parental OmpG from *E. coli* can share sequence identity with the OmpG from *E. coli*(SEQ ID NO:1 of at least 70%, at least 80%, at least 85%, at least 90%, at least 95%, at least 98%, or at least 99%. For example, a variant OmpG can be derived from a homolog of the *E. coli* OmpG that is at least 70%, at least 80%, at least 85%, at least 90%, at least 95%, at least 98%, or at least 99% identical to the parental OmpG from *E. coli*. In some embodiments, the parental OmpG is the OmpG from the *E. coli* sp. strain K12. The polypeptide sequence of the full length *E. coli* OmpG (SEQ ID NO:1) and examples of homologs from *Shigella flexneri* (SEQ ID NO: 12), *Salmonella enterica* (SEQ ID NOs:13 and 14), and *Citrobacter farmeri* (SEQ ID NO:15) are provided in FIG. 9. SEQ ID NO:2 is the mature form of the full-length *E. coli* OmpG polypeptide depicted in SEQ ID NO:1.

In some embodiments, the parental polypeptide is a wild-type OmpG polypeptide. In other embodiments, the parental polypeptide is an OmpG variant to which additional mutations can be introduced to improve the ability of the OmpG polypeptide to reduce ionic current noise. The variant OmpG retains the ability to form a nanopore. In one embodiment, the parental OmpG polypeptide is the wild-type *E. coli* OmpG polypeptide of SEQ ID NO:1, or the mature form thereof (SEQ ID NO:2). It is understood that the variant OmpG polypeptides can be expressed having the N-terminal Met.

In another embodiment, the parental OmpG polypeptide is a variant OmpG polypeptide from which the amino acids that comprise loop 6 are deleted. For example, the parental OmpG is the OmpG of SEQ ID NO:2 from which the amino acids that comprise loop 6 have been deleted. The OmpG of SEQ ID NO:3 is the mature form of the wild-type OmpG (SEQ ID NO:2) from which amino acids 216-227 have been deleted and amino acid 229 is replaced by an Ala, i.e., Δ216-227/E229A. SEQ ID NO:3 comprises a sequence of amino acids at the C-terminus that denotes the linker-His6-linker-SpyTag sequences ("His6" disclosed as SEQ ID NO: 18) as described elsewhere herein. Variant OmpGs comprising a deletion of loop 6 and substitution of Ala at amino acid 229, i.e., Δ216-227/E229A are interchangeably denoted by ΔL6/E229A. In some embodiments, truncation of loop 6 can be made by deleting one or more of amino acids 216-227 of SEQ ID NO:2. In other embodiments, amino acids 216-227, inclusive, are deleted. The numbering of the amino acids refers to the amino acid positions of SEQ ID NO: 2.

In one embodiment, the variant OmpG is a variant of the parental OmpG of SEQ ID NO:2 that comprises a deletion of amino acids 216-227, i.e., Δ216-227. In a further embodiment the variant OmpG comprises E229A, i.e., Δ216-227/E229A. In yet a further embodiment, the variant OmpG comprises a deletion of D215, i.e., Δ215-227/E229A.

Amino acids at the constriction zone of the OmpG pore (the smallest "choke point" of the nanopore) at the extracellular surface are identified as contributing to the symmetry of the lining and/or the length of the constriction of OmpG. In some embodiments, the constriction zone amino acids can be mutated to shorten the length of the constriction and/or even the width of the internal diameter of the constriction. Mutagenesis of the constriction amino acids can be designed to create a unique constriction zone. Mutations of the constriction zones reduce the ion current noise of the variant OmpG when compared to the parental OmpG from which the variant is derived. Accordingly, in some embodiments, the variant OmpG polypeptide provided comprises one or more mutations of amino acids that are positioned at the constriction zone at the extracellular side of the OmpG nanopore. In other embodiments, the variant OmpG polypeptide can be further mutated to bind molecular adaptors, which while resident in the pore, slow the movement of analytes, e.g., nucleotide bases, through the pore and consequently improve the accuracy of the identification of the analyte (Astier et al., *J Am Chem Soc* 10.1021/ja057123+, published online on Dec. 30, 2005).

In some embodiments, the mutation in the constriction zone, e.g., mutation of the OmpG depicted in SEQ ID NO:2, is selected from amino acids R211, E15, R68, Y50, E152, E174, E17, D215, Y259, K114, E174, F66, and/or E31. A mutation of the amino acids at the constriction zone can be one or more of a substitution, a deletion or an insertion, for example, a substitution of one or more of amino acids R211, E15, R68, Y50, E152, E174, E17, D215, Y259, K114, E174, F66, and/or E31. In some embodiments, at least one amino acid mutation is located in the constriction zone of OmpG. In other embodiments, at least two, at least three, at least four, at least five, or at least six amino acids of the constriction zone are mutated. In some embodiments, the at least one amino acid mutation at the constriction zone is the substitution Y50K. In some other embodiments, the at least one amino acid mutation at the constriction zone is the substitution Y50N. The at least one amino acid mutation at the constriction zone can be combined with the deletion of one or more of the amino acids of loop 6. Thus, in some embodiments, the variant OmpG is derived from a parental OmpG, e.g., the OmpG depicted in SEQ ID NO:2, and comprises a deletion of amino acids 216-227 and substation of Ala at amino acid 229, i.e., Δ216-227/E229A, and a mutation of at least one amino acid of the constriction zone of the wild-type OmpG, e.g., a mutation of one or more of amino acids R211, E15, R68, Y50, E152, E174, E17, D215, Y259, K114, E174, F66, and/or E31. In other embodiments, the variant OmpG comprises a deletion of loop 6, a mutation of one or more amino acids at the constriction zone, and the deletion D215. For example, the variant OmpG is a variant of a parental OmpG of SEQ ID NO:2, and comprises a deletion of amino acids 216-227 and substitution of Ala at amino acid 229, i.e., Δ216-227/E229A, a mutation of at least one of amino acids of the constriction zone, e.g., a mutation of one or more of amino acids R211, E15, R68, Y50, E152, E174, E17, D215, Y259, K114, E174, F66, and/or E31, and del215. In one embodiment, the variant OmpG is a variant of a parental OmpG of SEQ ID NO:2, and comprises a deletion of amino acids 216-227, i.e., Δ216-227, substitution E229A, deletion of D215, and amino acid substitution Y50K.

Figure 10A:
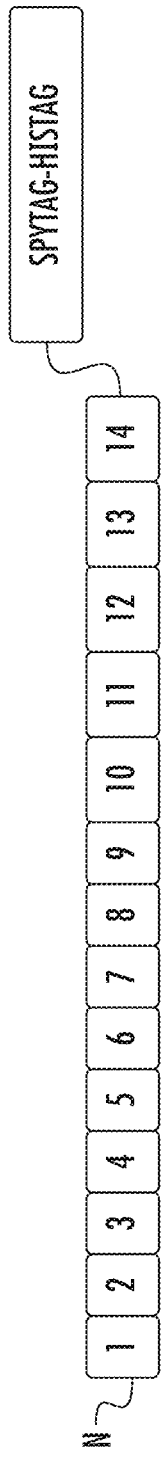
FIGS. 10A-10B schematically depict OmpG antiparallel β-strands (FIG. 10A) and an embodiment of a circular permutation variant thereof (FIG. 10B).
Figure 10B:
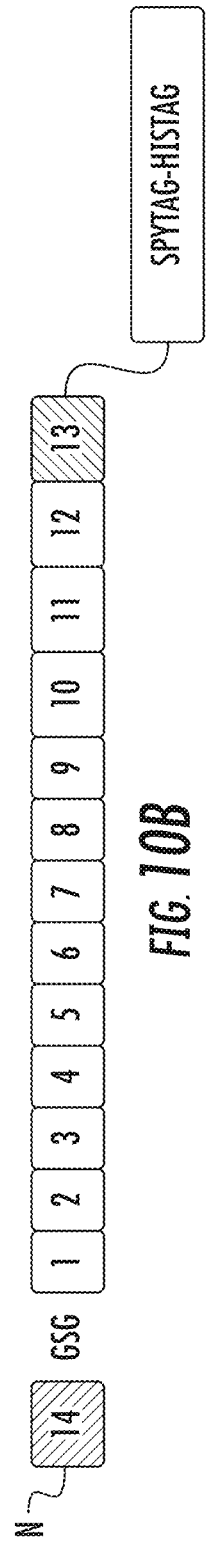
Figure 11:
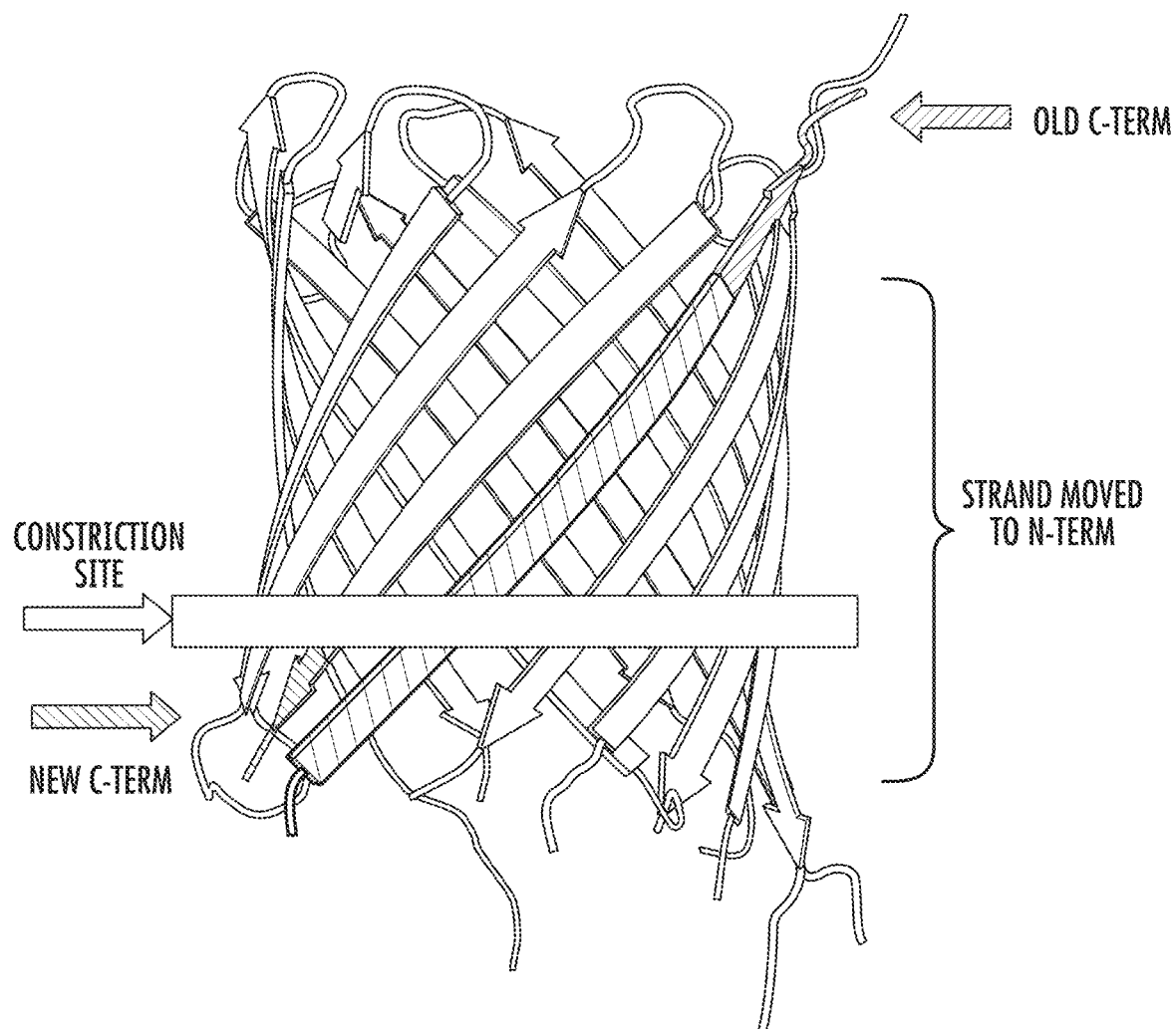
FIG. 11 shows the arrangement of the C-terminus of OmpG in the wild-type parental OmpG versus the circular permutation variant as described herein, relative to the constriction site of the nanopore protein.

In some embodiments, a "circular permutation variant of OmpG is provided wherein the C-terminal β-strand of the parental OmpG is moved to the N-terminus of the protein sequence, retaining the penultimate β-strand of the parental OmpG as the new C-terminus of the protein. This is depicted schematically in FIGS. 10 and 11. The result of movement of the C-terminal β-strand in this manner is that the new C-terminus of the variant is closer to the constriction site of the nanopore than in the parental OmpG from which the variant was derived (see FIG. 11). The proximity to the constriction point is advantageous because it allows for improved capture of molecules for analysis by the nanopore. This improved capture may be due to a reduction in the energy barrier of NanoTag threading. The placement of the N-terminus and C-terminus on opposite sides of the lipid or polymer layer also allows for the attachment of two nucleic acid modifying enzymes, doubling the throughput of the nanopore-based instrument.

Optionally, a circular permutation variant as described herein includes a tag sequence (e.g., comprising a "SpyTag" or "His-SpyTag" sequence, optionally further comprising one or more linker sequences (e.g., SEQ ID NO:16) at the C-terminus, downstream from the penultimate β-strand of the parental OmpG. Optionally, the variant includes a linker sequence, e.g., GSG, between the new N-terminal β-strand that was moved from the C-terminus of the parental OmpG and the β-strand that was previously at the N-terminus of the parental OmpG. In one embodiment, the variant is a variant of the *E. coli* OmpG depicted in SEQ ID NO:2, or a homolog thereof. In one embodiment, the variant comprises movement of amino acid residues 267-280 of SEQ ID NO:2 to the N-terminus of SEQ ID NO:2, optionally with a linker, e.g., GSG, between previous residue 280 and the N-terminus of SEQ ID NO:2, and optionally with a methionine (M) residue at the N-terminus of the variant, prior to previous residue 267, and optionally with the amino acid sequence depicted in SEQ ID NO:16 at the C-terminus of the variant. In one embodiment, the variant has the amino acid sequence depicted in SEQ ID NO: 17.

DNA Sequence Encoding OmpG Variants

DNA sequences encoding a parent OmpG may be isolated from any cell or microorganism producing the OmpG in question, using various methods well known in the art. First, a genomic DNA and/or cDNA library can be constructed using chromosomal DNA or messenger RNA from the organism that produces the OmpG to be studied. Then, if the amino acid sequence of the OmpG is known, homologous, labeled oligonucleotide probes may be synthesized and used to identify OmpG-encoding clones from a genomic library prepared from the organism in question. Alternatively, a labeled oligonucleotide probe containing sequences homologous to a known OmpG gene can be used as a probe to identify OmpG-encoding clones, using hybridization and washing conditions of lower stringency.

Alternatively, the DNA sequence encoding the OmpG may be prepared synthetically by established standard methods, e.g., the phosphoroamidite method described by S. L. Beaucage and M. H. Caruthers (1981) *Tetrahedron Letters* 22:1859-1862 or the method described by Matthes et al. (1984) *EMBO J.* 3(4):801-5. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988) Science 239(4839):489-91.

Site-Directed Mutagenesis

Once an OmpG-encoding DNA sequence has been isolated, and desirable sites for mutation have been identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the OmpG-encoding sequence, or portion thereof, is created in a vector carrying the OmpG gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984) Nature Biotechnology 2:636-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced. Other methods that effect site-directed mutagenesis include Kunkel's method, cassette mutagenesis, and PCR site-directed mutagenesis. Alternative methods for providing variants include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

Expression of OmpG Variants

A DNA sequence encoding an OmpG variant can be used to express a variant OmpG, using an expression vector, which typically includes control sequences encoding a promoter, an operator, a ribosome binding site, a translation initiation signal, and, optionally, a repressor gene or various activator genes. Examples of vectors that can be used for expressing variant OmpGs include the vectors of the pET expression system (Novagen).

A recombinant expression vector carrying DNA sequences encoding an OmpG variant may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, a minichromosome or an artificial chromosome. Alternatively, the vector may be one which, when introduced into a host cell, is integrated into the host cell genome and replicates together with the chromosome(s) into which it has been integrated.

The procedures used to ligate the DNA construct encoding an OmpG variant, and to insert it into suitable vectors containing the information necessary for replication, are well known to persons skilled in the art (cf., for instance, Sambrook et al., *Molecular Cloning: A Laboratory Manual*, Fourth Edition, Cold Spring Harbor, 2012).

An OmpG variant can be produced in a cell that may be of a higher organism such as a mammal or an insect, but is preferably a microbial cell, e.g., a bacterial or a fungal (including yeast) cell. Examples of suitable bacteria are gram-negative bacteria such as *E. coli*, or gram-positive bacteria such as *Bacillus* sp., e.g., *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulars, Bacillus lautus, Bacillus megaterium,* or *Bacillus thuringiensis*, or *Streptomyces* sp., e.g., *Streptomyces lividans* or *Streptomyces murinus*. A yeast organism may be selected from a species of *Saccharomyces* or *Schizosaccharomyces*, e.g., *Saccharomyces cerevisiae*, or from a filamentous fungus, such as *Aspergillus* sp., e.g., *Aspergillus* oyzae or *Aspergillus niger*. The host cell is typically bacterial and preferably *E. coli*.

In a further aspect, a method of producing an OmpG variant is provided, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the OmpG variant. Suitable media are available from commercial suppliers or may be prepared according to published recipes (e.g., as described in catalogues of the American Type Culture Collection).

The OmpG variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like. In some embodiments, purification of the variant OmpG may be obtained by affinity chromatography of OmpG polypeptides linked to an affinity tag. Several affinity or epitope tags that can be used in the purification of the OmpG variants include hexahistidine tag (SEQ ID NO: 18), FLAG tag, Strep II tag, streptavidin-binding peptide (SBP) tag, calmodulin-binding peptide (CBP), glutathione S-transferase (GST), maltose-binding protein (MBP), S-tag, HA tag, and c-Myc tag. In some embodiments, a hexahistidine tag (SEQ ID NO: 18) is used in the purification of OmpG. The affinity tag can be covalently attached to the variant OmpG polypeptide by a protein linker. Specific linkers contemplated as useful in linking the nanopore to a polymerase include $(GGGGS)_{1-3}$ (SEQ ID NO: 19), EKEKEKGS (SEQ ID NO: 20), His6-GSGGK (SEQ ID NO: 21), and AHIVMVDAYKPTK (SEQ ID NO: 22) (SpyTag). The protein linkers can be encoded by the nucleic acid that comprises the sequence encoding the variant OmpG, and may be expressed as a fusion protein. For example, the variant OmpG can be expressed as OmpG-$(EK)_3$-Hiss-GSGG-SpyTag (EK EKEKGSHHHH HHGSG-GAHIV MVDAYKPTK (SEQ ID NO:16)) expressed for example, as amino acids 269-299 of SEQ ID NO:3. In some instance, the Hiss tag (SEQ ID NO: 18) is expressed N-terminal to the variant OmpG polypeptide.

Nanopore Assembly

Characterization of the variant OmpG can include determining any property of the molecule that causes a variance in a measurable electrical signature. For example, reduction in gating frequency may be derived from measuring a decrease in upward and/or downward gating through the nanopore as a constant voltage is applied across the variant OmpG nanopore. Additionally, characterization of the variant OmpG can include identifying tags of individual tagged nucleotides which are complementary to a DNA or RNA strand by measuring a variance in ionic current flow through the nanopore as the tags of individual nucleotides are detected in proximity or in passing through the OmpG nanopore. The base sequence of a segment of a DNA or RNA molecule can be determined by comparing and correlating the measured electrical signature(s) of tags of tagged nucleotides, as the growing nucleic acid strand is synthesized.

Typically, measurements of ionic current flow through the OmpG nanopore are made across nanopores that have been reconstituted into a lipid membrane. In some instances, the OmpG nanopore is inserted in the membrane (e.g., by electroporation). The nanopore can be inserted by a stimulus signal such as electrical stimulus, pressure stimulus, liquid flow stimulus, gas bubble stimulus, sonication, sound, vibration, or any combination thereof. In some cases, the membrane is formed with aid of a bubble and the nanopore is inserted in the membrane with aid of an electrical stimulus.

Methods for assembling a lipid bilayer, forming a nanopore in a lipid bilayer, and sequencing nucleic acid molecules can be found in PCT Patent Publication Nos. WO2011/097028 and WO2015/061510, which are incorporated herein by reference in their entirety.

FIG. 2 is a schematic diagram of a nanopore device 100 that can be used to characterize a polynucleotide or a polypeptide. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer comprising the nanopore can be disposed over a well, where a sensor forms part of the surface of the well. Descriptions of the location of nanopores in lipid bilayers over wells can be found, for example, in WO2015/061509. The lipid bilayer 102 is embedded with a single nanopore structure 108 having a nanopore 110 large enough for passing of at least a portion of the molecule 112 being characterized and/or small ions (e.g., $Na^+$, $K^+$, $Ca^{2+}$, $Cl^-$) between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the molecule 112 may be provided over the lipid bilayer 102 for introducing the molecule 112 for characterization. The solution may be an aqueous solution containing electrolytes and buffered to an optimum ion concentration and maintained at an optimum pH to keep the nanopore 110 open. The device includes a pair of electrodes 118 (including a negative node 118a and a positive node 118b) coupled to a variable voltage source 120 for providing electrical stimulus (e.g., voltage bias) across the lipid bilayer and for sensing electrical characteristics of the lipid bilayer (e.g., resistance, capacitance, and ionic current flow). The surface of the positive electrode 118b is or forms a part of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the variable voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

In one example, the nanopore device 100 of FIG. 2 is an OmpG nanopore device having a single OmpG protein 108, e.g., a variant OmpG as described herein, embedded in a lipid bilayer 102 formed over a lipid bilayer compatible silver-gold alloy surface 104 coated on a copper material 106. The lipid bilayer compatible silver-gold alloy surface 104 is isolated by lipid bilayer incompatible silicon nitride surfaces 105, and the copper material 106 is electrically insulated by silicon nitride materials 107. The copper 106 is coupled to electrical circuitry 122 that is integrated in a silicon substrate 128. A silver-silver chloride electrode placed on-chip or extending down from a cover plate 128 contacts an aqueous solution containing dsDNA molecules.

The lipid bilayer may comprise or consist of phospholipid, for example, selected from diphytanoyl-phosphatidyl-choline (DPhPC), 1,2-diphytanoyl-sn-glycero-3phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

Figure 3A:
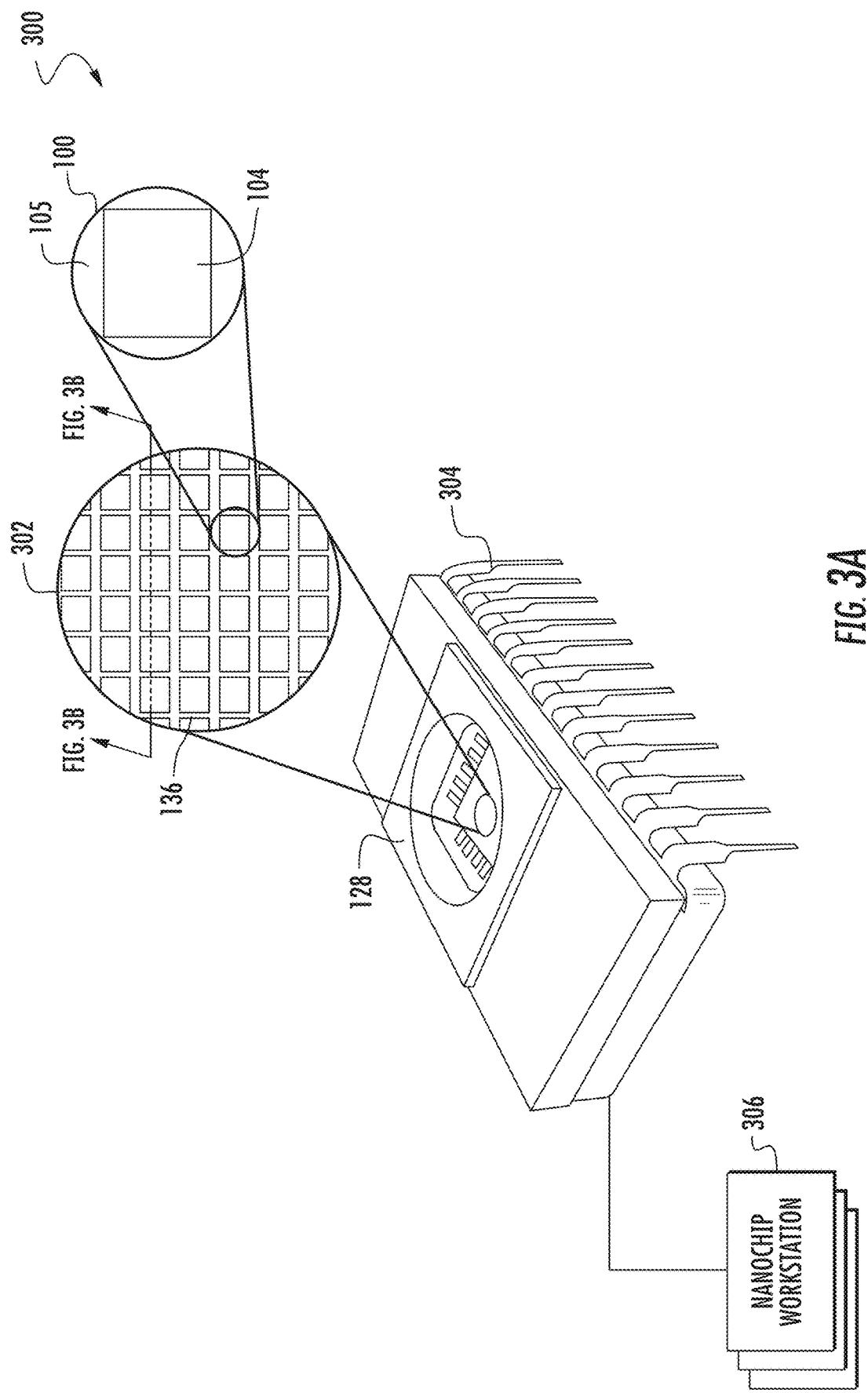
FIGS. 3A-3B show a schematic diagram of an embodiment of a chip that includes a nanopore device array. A perspective view is shown in FIG. 3A. A cross-sectional view of the chip is shown in FIG. 3B.
Figure 3B:
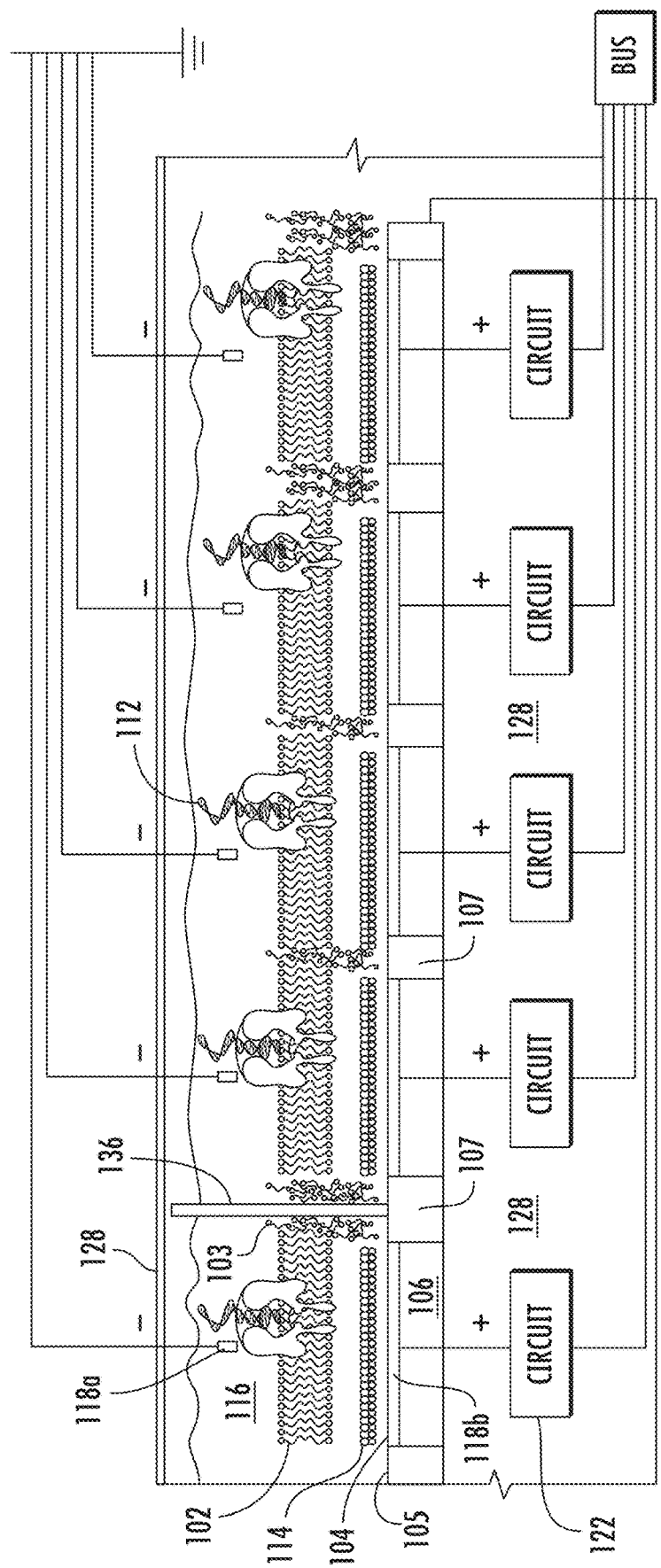
Figure 4A:
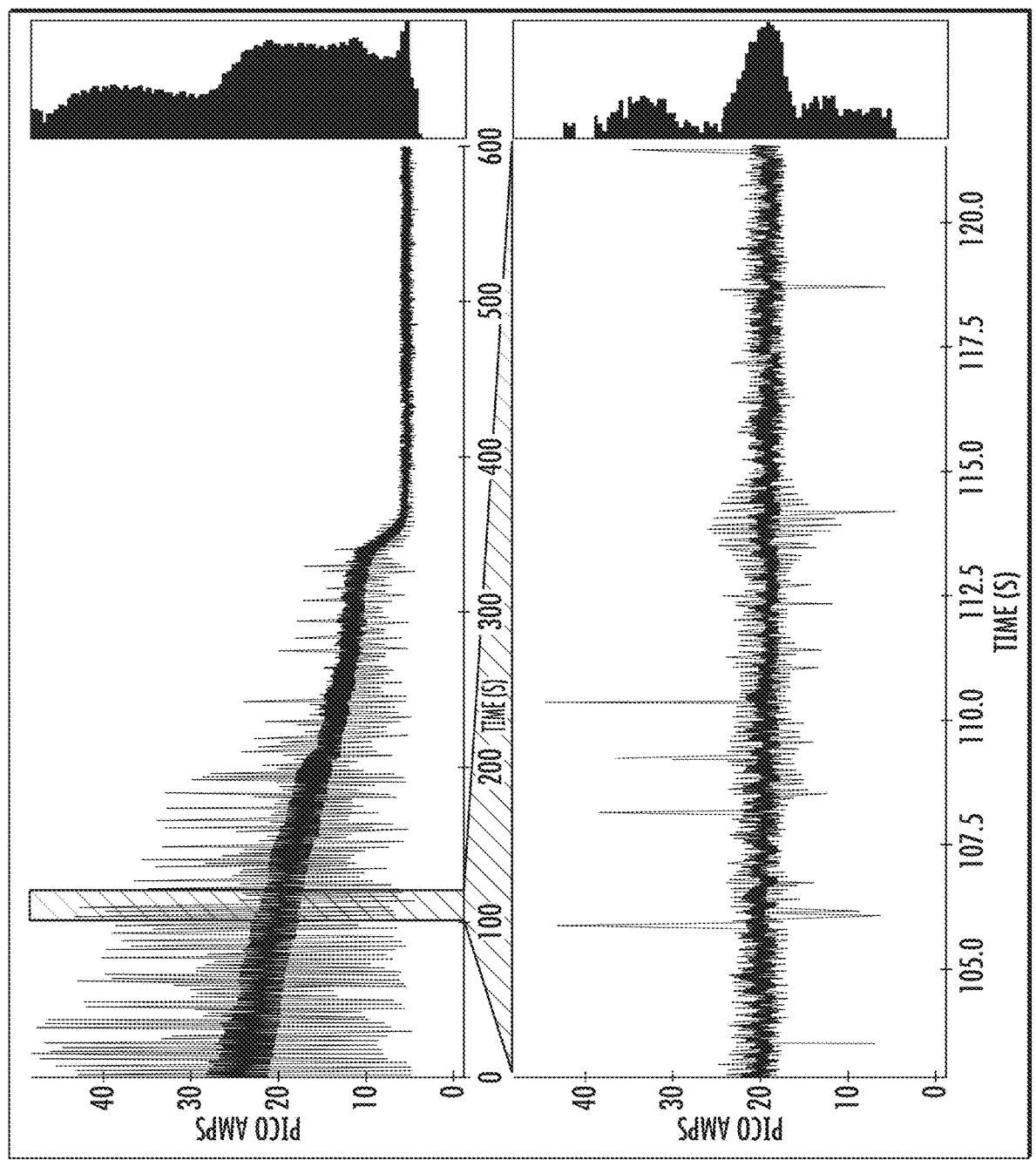
FIGS. 4A-4E depict single channel current traces obtained at an applied constant voltage for OmpG variants comprising a deletion of amino acids 216-227, and amino acid substitution E229A (ΔL6/E229A) (as shown in (SEQ ID NO:5)), and the amino acid substitution Y50K (SEQ ID NO:6.
Figure 4B:
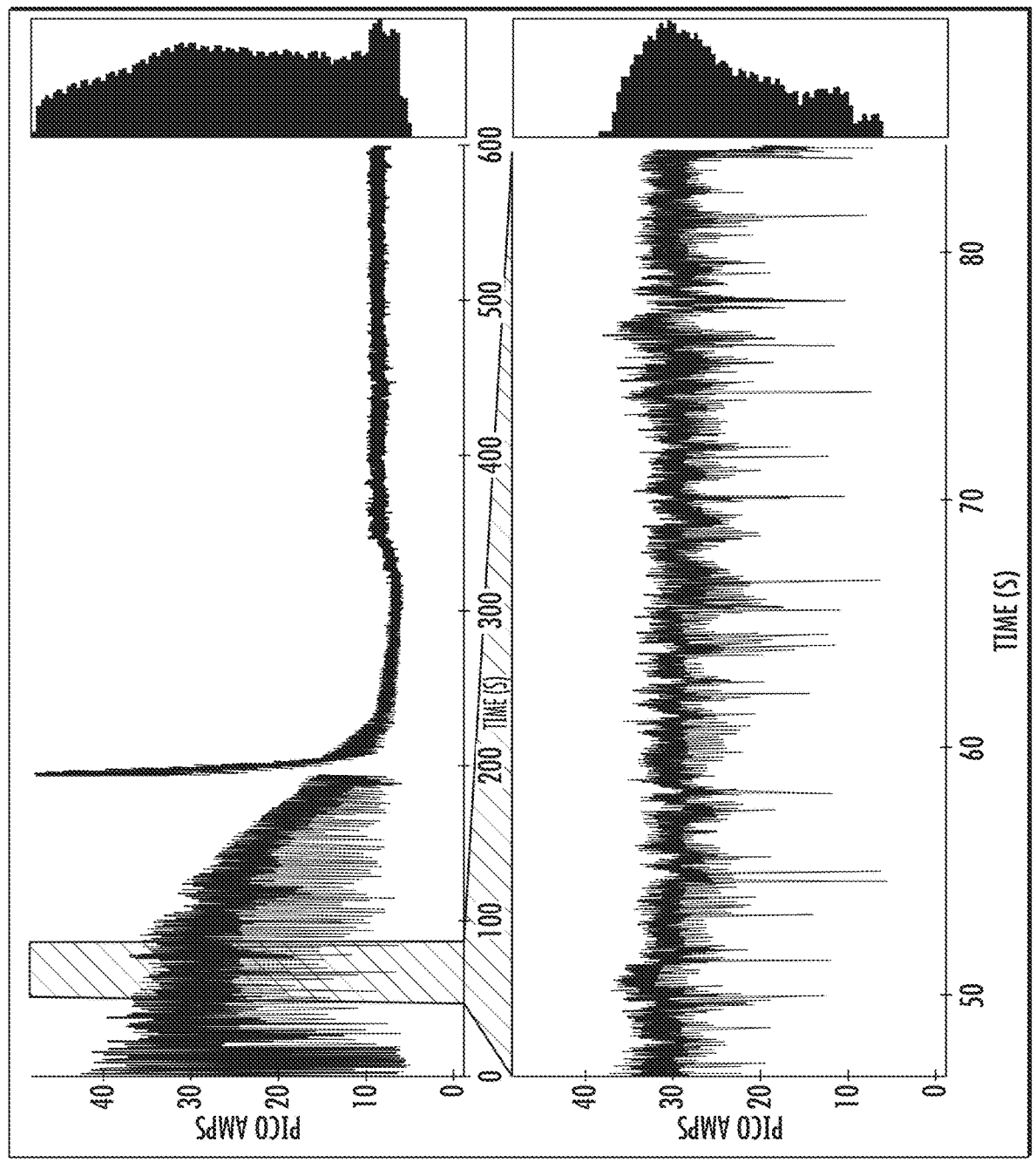
Figure 4C:
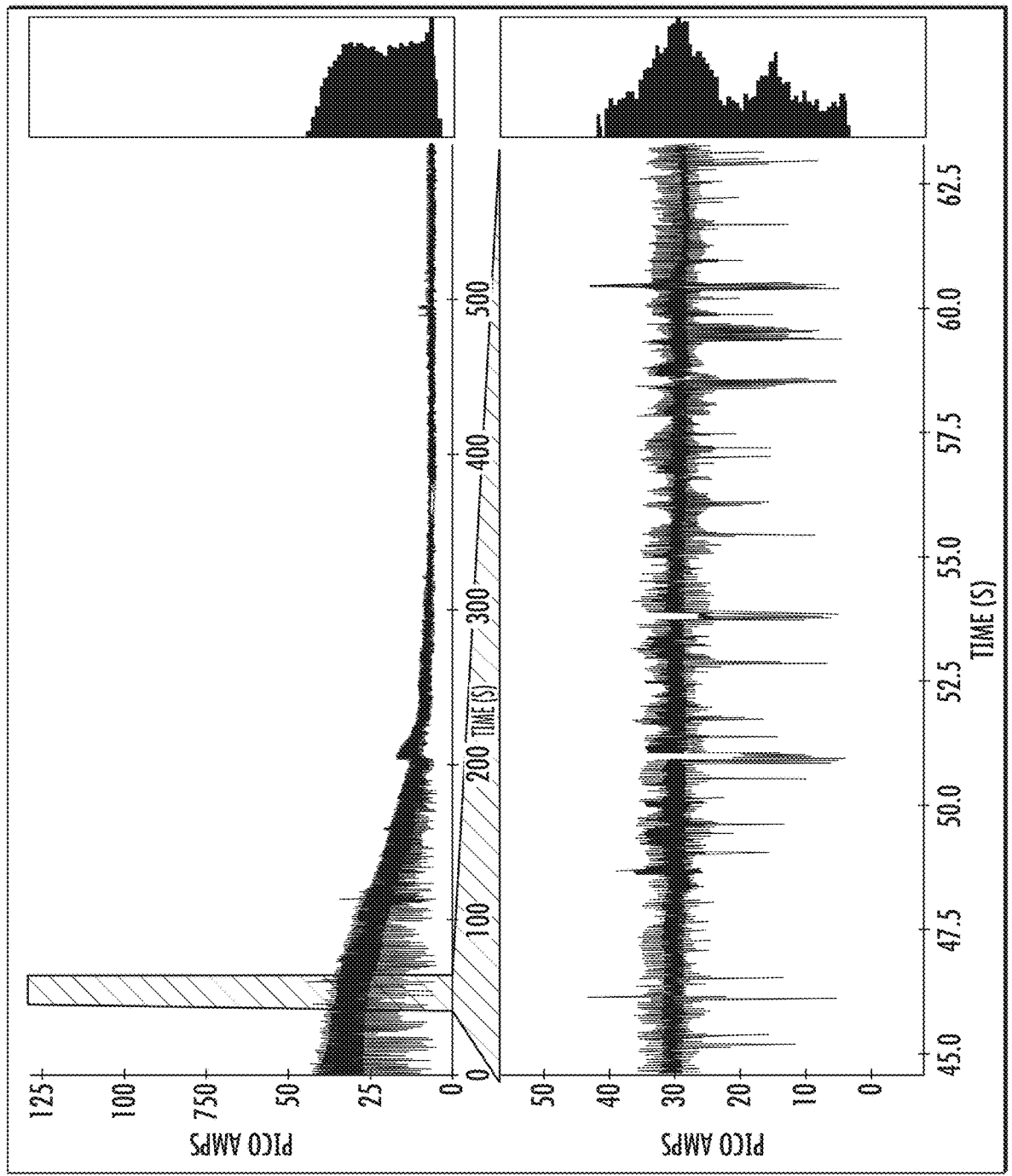
Figure 4D:
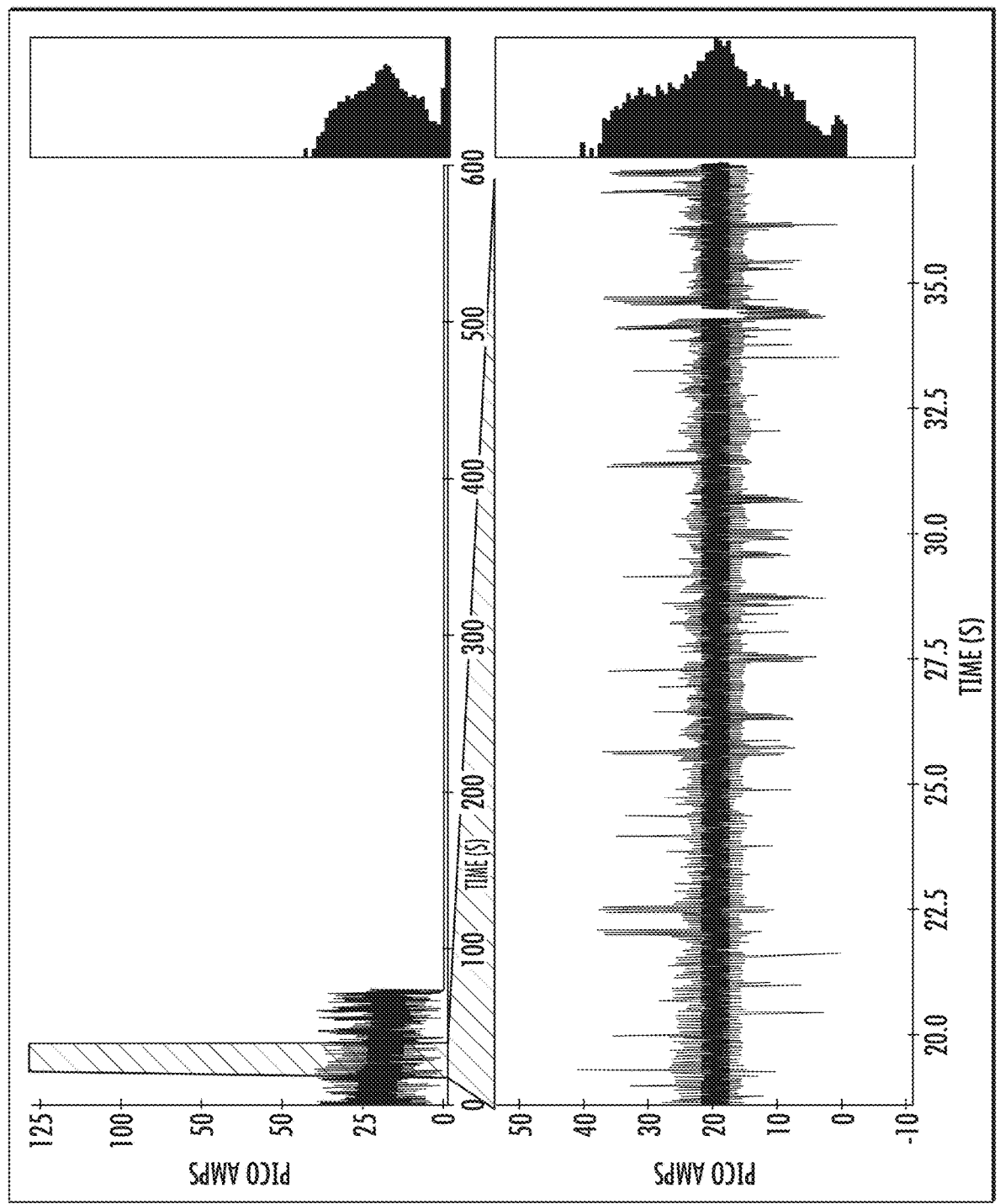
Figure 4E:
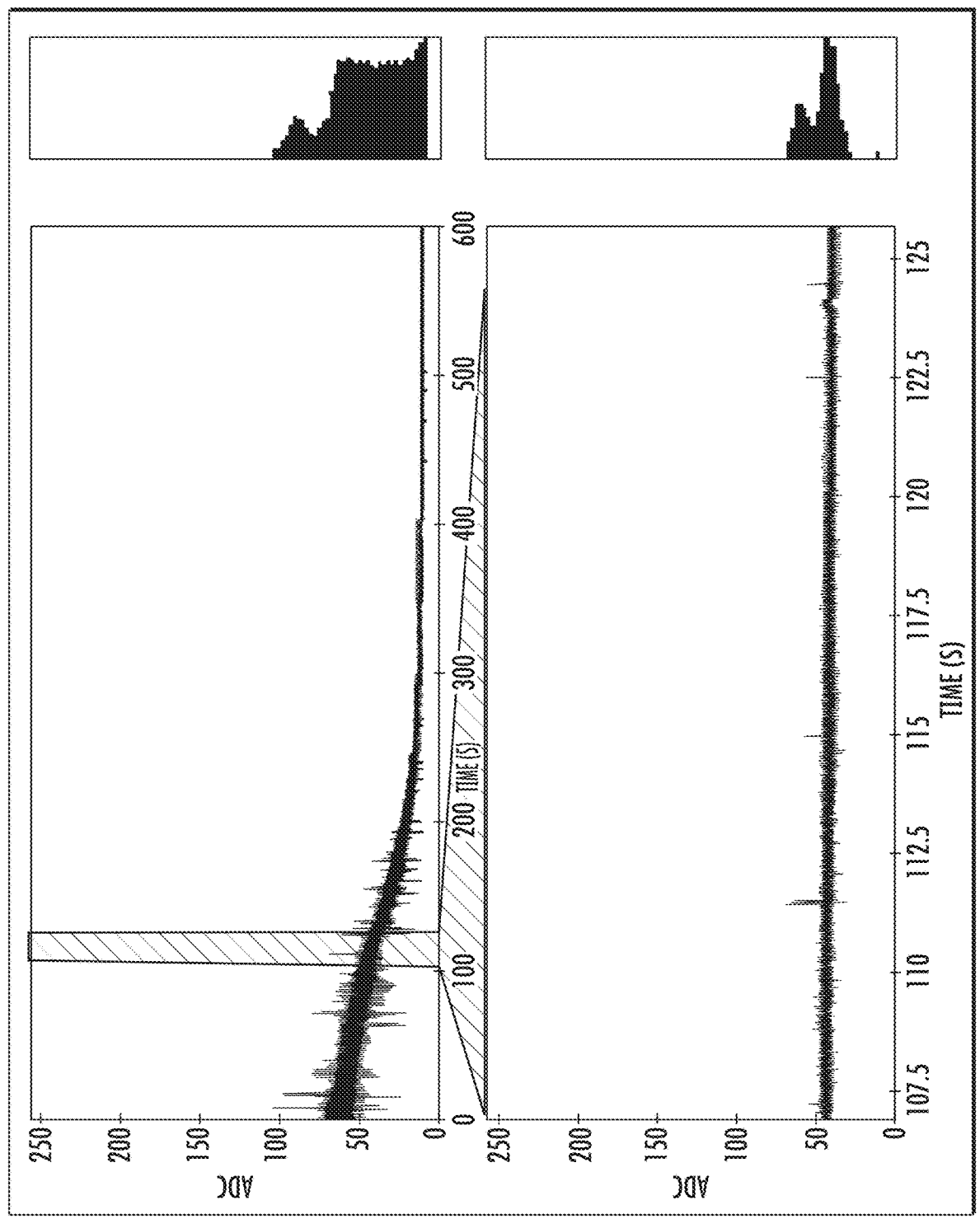

The nanopores can form an array. The disclosure provides an array of nanopore detectors (or sensors). FIG. 3A is a top view of a schematic diagram of an embodiment of a nanopore chip 300 having an array 302 of individually addressable nanopore devices 100 having a lipid bilayer compatible surface 104 isolated by lipid bilayer incompatible surfaces 105. Each nanopore device 100 is complete with a control circuit 122 integrated on a silicon substrate 128. In some embodiments, side walls 136 may be included to separate groups of nanopore devices 100 so that each group may receive a different sample for characterization. In some embodiments, the nanopore chip 300 may include a cover plate 128. The nanopore chip 300 may also include a plurality of pins 304 for interfacing with a computer processor. In some embodiments, the nanopore chip 300 may be coupled to (e.g., docked to) a nanopore workstation 306, which may include various components for carrying out (e.g., automatically carrying out) the various embodiments of the processes of the present invention, including for example, analyte delivery mechanisms such as pipettes for delivering lipid suspension, analyte solution, and/or other liquids, suspension or solids, robotic arms, computer processor, and/or memory. FIG. 3B is a cross sectional view of the nanopore chip 300. With reference to FIGS. 3A and 3B, a plurality of polynucleotides may be detected on an array of nanopore detectors. Here, each nanopore location comprises a nanopore, in some cases attached to a polymerase enzyme as described elsewhere herein. Each of the nanopores can be individually addressable.

The methods of the invention involve the measuring of a current passing through the pore during interaction with a nucleotide. In some embodiments, sequencing a nucleic acid molecule can require applying a direct current (e.g., so that the direction at which the molecule moves through the nanopore is not reversed). However, operating a nanopore sensor for long periods of time using a direct current can change the composition of the electrode, unbalance the ion concentrations across the nanopore and have other undesirable effects. Applying an alternating current (AC) waveform can avoid these undesirable effects and have certain advantages as described below. The nucleic acid sequencing methods described herein that utilize tagged nucleotides are fully compatible with AC applied voltages, and AC can therefore be used to achieve said advantages.

Suitable conditions for measuring ionic currents through transmembrane protein pores are known in the art and examples are provided herein in the Experimental section. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore of the invention by using an increased applied potential. Sequencing nucleic acids using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymidine (Horhota et al. *Organic Letters*, 8:5345-5347 [2006]).

Nanopore-Polymerase Complex

In some cases, a polymerase (e.g., DNA polymerase) is attached to and/or is located in proximity to the nanopore. The polymerase can be attached to the nanopore before or after the nanopore is incorporated into the membrane. In some cases, the polymerase is attached to the OmpG protein monomer and then the nanopore polymerase complex can then be inserted into the membrane.

An exemplary method for attaching a polymerase to a nanopore involves attaching a linker molecule to an OmpG monomer or mutating the OmpG to have an attachment site or attachment linker, and then attaching a polymerase to the attachment site or attachment linker (e.g., in bulk, before inserting into the membrane). The polymerase can also be attached to the attachment site or attachment linker after the nanopore is formed in the membrane. In some cases, a plurality of nanopore-polymerase pairs is inserted into a plurality of membranes (e.g., disposed over the wells and/or electrodes) of a biochip, thereby forming a nanopore chip as described herein. In some instances, the attachment of the polymerase to the nanopore to form a nanopore-polymerase complex occurs on the biochip above each electrode.

The polymerase can be attached to the nanopore with any suitable chemistry (e.g., covalent bond and/or linker). In some instances, the polymerase is expressed as a fusion protein that comprises a SpyCatcher polypeptide, which can be covalently bound to an OmpG nanopore that comprises a SpyTag peptide. In some instances, the polymerase is attached to the nanopore with molecular staples. In some instances, molecular staples comprise three amino acid sequences (denoted linkers A, B and C). Linker A can extend from an OmpG polypeptide, Linker B can extend from the polymerase, and Linker C then can bind Linkers A and B (e.g., by wrapping around both Linkers A and B) and thus bind the polymerase to the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the OmpG molecule and then a molecule is used (e.g., a DNA intermediate molecule) to link the polymerase to the zinc finger sites on the OmpG.

Other linkers that may find use in attaching the polymerase to a nanopore are direct genetic linkage (e.g., (GGGGS)$_{1-3}$ amino acid linker (SEQ ID NO: 19)), transglutaminase mediated linking (e.g., RSKLG (SEQ ID NO: 23)), sortase mediated linking, and chemical linking through cysteine modifications. Specific linkers contemplated as useful herein are (GGGGS)$_{1-3}$ (SEQ ID NO: 19), K-tag (RSKLG (SEQ ID NO: 23)) on N-terminus, ΔTEV site (12-25), ΔTEV site+N-terminus of SpyCatcher (12-49).

The polymerase may be coupled to the nanopore by any suitable means. See, for example, PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

In some instances, the nanopore and polymerase are produced as a fusion protein (i.e., single polypeptide chain), and are incorporated into the membrane as such.

The polymerase can be mutated to reduce the rate at which the polymerase incorporates a nucleotide into a nucleic acid strand (e.g., a growing nucleic acid strand). In some cases, the rate at which a nucleotide is incorporated into a nucleic acid strand can be reduced by functionalizing the nucleotide and/or template strand to provide steric hindrance, such as, for example, through methylation of the template nucleic acid strand. In some instances, the rate is reduced by incorporating methylated nucleotides.

Methods for Sequencing Polynucleotides

The molecules being characterized using the variant OmpG polypeptides described herein can be of various types, including charged or polar molecules such as charged or polar polymeric molecules. Specific examples include ribonucleic acid (RNA) and deoxyribonucleic acid (DNA) molecules. The DNA can be a single-strand DNA (ssDNA) or a double-strand DNA (dsDNA) molecule.

In one aspect, provided are methods for sequencing nucleic acids using the instant OmpG variant nanopores. The OmpG variants provided in the present disclosure can be used for determining the sequence of nucleic acids according to other nanopore sequencing platforms known in the art. For example, the OmpG variant provided in this disclosure may be suitable for sequencing nucleic acids according to the exonuclease-based method of Oxford Nanopore (Oxford, UK), the nanopore-based sequencing-by-hybridization of NABsys (Providence, RI), the fluorescence-based optical nanopore sequencing of NobleGen Biosciences (Concord, MA), Illumina (San Diego, CA), and the nanopore sequencing-by-expansion of Stratos Genomics (Seattle, WA). In some embodiments, sequencing of nucleic acids using the OmpG variants can be performed using tagged nucleotides as is described in PCT/US2013/068967 (entitled "Nucleic Acid Sequencing Using Tags" filed on Nov. 7, 2013, which is herein incorporated by reference in its entirety). For example, a variant OmpG nanopore that is situated in a membrane (e.g., a lipid bilayer) adjacent to or in sensing proximity to one or more sensing electrodes, can detect the incorporation of a tagged nucleotide by a polymerase as the nucleotide base is incorporated into a polynucleotide strand and the tag of the nucleotide is detected by the nanopore. The polymerase can be associated with the nanopore as described above.

Tags of the tagged nucleotides can include chemical groups or molecules that are capable of being detected by a nanopore. Examples of tags used to provide tagged nucleotides are described at least at paragraphs to of PCT/US2013/068967. Nucleotides may be incorporated from a mixture of different nucleotides, e.g., a mixture of tagged dNTPs where N is adenosine (A), cytidine (C), thymidine (T), guanosine (G) or uracil (U). Alternatively, nucleotides can be incorporated from alternating solutions of individual tagged dNTPs, i.e., tagged dATP followed by tagged dCTP, followed by tagged dGTP, etc. Determination of a polynucleotide sequence can occur as the nanopore detects the tags as they flow through or are adjacent to the nanopore, as the tags reside in the nanopore and/or as the tags are presented to the nanopore. The tag of each tagged nucleotide can be couple to the nucleotide base at any position including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the tagged nucleotides, and the tags pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and may be detected with the aid of the nanopore.

In some cases, tagged nucleotides that are not incorporated pass through the nanopore. The method can distinguish between tags associated with un-incorporated nucleotides and tags associated with incorporated nucleotides based on the length of time the tagged nucleotide is detected by the nanopore. In one embodiment, an un-incorporated nucleotide is detected by the nanopore for less than about 1 millisecond and an incorporated nucleotide is detected by the nanopore for at least about 1 millisecond.

Thus, in one aspect, the disclosure provides for a method for sequencing a nucleic acid with the aid of a variant OmpG nanopore. In one embodiment, a method is provided for sequencing a nucleic acid with the aid of a variant OmpG nanopore adjacent to a sensing electrode by (a) providing tagged nucleotides into a reaction chamber comprising the nanopore, wherein an individual tagged nucleotide of the tagged nucleotides contains a tag coupled to a nucleotide, which tag is detectable with the aid of the nanopore; (b) carrying out a polymerization reaction, with the aid of a polymerase, thereby incorporating an individual tagged nucleotide of the tagged nucleotides into a growing strand complementary to a single stranded nucleic acid molecule from the nucleic acid sample; and (c) detecting, with the aid of the nanopore, a tag associated with the individual tagged nucleotide during and/or upon incorporation of the individual tagged nucleotide, wherein the tag is detected with the aid of the nanopore when the nucleotide is associated with the polymerase. Other embodiments of the sequencing method that comprise the use of tagged nucleotides with the present variant OmpG nanopores for sequencing polynucleotides are provided in WO2014/074727, which is incorporated herein by reference in its entirety.

EXAMPLES

Example 1

Expression and Purification of OmpG-EXT

A DNA encoding a form of the mature OmpG protein (residues 22-301; Uniprot entry P76045) lacking loop 6 and having substitution E229A (OmpG-EXT) was synthesized (Genscript, NJ) based on the ΔL6II construct described by Grosse et al. (*Biochemistry* 53:4826-4838 [2014]). The synthetic DNA (OmpG-ΔL6/E229A) encodes an OmpG construct having a deletion of loop 6 and a C-terminal sequence: linker1-His tag-linker2-Spytag (SEQ ID NO:3). A synthetic DNA sequence derived from the wild-type sequence (SEQ ID NO:4) and encoding the truncation of loop 6 (ΔL6) and substitution E229A, was cloned in the pET-26b vector and produced in OmpG-deficient BI21 DE3 *E. coli* (www.neb.com/products/c2527-bl21de3-competent-*E-coli*) as inclusion bodies.

Expression of OmpG-ΔL6/E229A was obtained by IPTG-induced transcription of the OmpG-ΔL6/E229A DNA in BI21 DE3 *E. coli* cells growing in MagicMedia™ (Invitrogen, Carlsbad, CA) for approximately 24 hours. The cells were centrifuged then resuspended in 50 mM Tris, PH8.0 (5 ml buffer to 1 g cell pellet). Next, the cells were sonicated, and the lysate centrifuged (10,000×g/20 min/4° C.). The pellet was washed twice by centrifugation and resuspension, and the final pellet was resuspended in 50 mM Tris pH8.0 at a concentration of 200 mg/ml. The inclusion bodies were aliquoted and stored at −80° C.

The inclusion bodies were solubilized in 50 mM Tris pH8.0, 6 M urea, and 2.4 mM TCEP at 60° C. for 10 minutes. Unsolubilized inclusion bodies were removed by centrifugation, and the solubilized protein present in the supernatant was diluted to 1 mg/ml in refolding buffer (25 mM Tris, pH8.0, 1.8M urea, 1 mM TCEP, and 3% β-OG). The OmpG-ΔL6/E229A protein was refolded for 16 hours at 37° C., then diluted using 50 mM Tris, pH8.0, 200 mM NaCl, 5 mM imidazole 1% β-OG to obtain a final concentration of 1% β-OG and 0.8M urea. The refolded protein was purified by affinity chromatography using TALON® (Clontech, Mountain View, CA), and eluted in 50 mM Tris, pH8.0, 200 mM NaCl, 200 mM imidazole, and 0.1% Tween-20. TALON is an immobilized metal affinity chromatography (IMAC) resin charged with cobalt, which binds to his-tagged proteins with higher specificity than nickel-charged resins.

Variants of the OmpG-ΔL6/E229A protein were obtained by site-directed mutagenesis on the basis of the DNA encoding the OmpG-ΔL6/E229A construct in the pET-26b vector. All OmpG-ΔL6/E229A variants were expressed and purified as described for OmpG-ΔL6 as described above.

Example 2

Characterization of OmpG Variants

To demonstrate the ability of the variant OmpG polypeptides to reduce spontaneous gating, individual variants were reconstituted as pores in a lipid bilayer over a well on a semiconductor sensor chip (a), and single channel recordings obtained for each of the OmpG variant pores (b).

(a) Reconstitution of OmpG Variants into Lipid Bilayers

Variant OmpG proteins comprising the deletion of loop 6 (ΔL6), and amino acid substitution E229A, i.e., ΔL6/E229A, in combination with one of amino acid substitutions selected from Y50K, Y50N, R68N, R211N, or E17K, and/or in combination with deletion of D215, were expressed and purified as described in Example 1. The lipid bilayer was formed and the nanopore was inserted as described in PCT/US2014/061853 (entitled "Methods for Forming Lipid Bilayers on Biochips" and filed 22 Oct. 2014).

(b) Single-Channels Recordings in Lipid Bilayers

To determine the effect of the mutations on current flow, single channel recordings were made for currents passing through variants of the OmpG-EXT nanopore. Measurements of ionic current flow through the OmpG nanopore were made using DC.

Chambers were filled with 20 mM HEPES, pH 8.0, 300 mM NaCl, 3 mM CaCl$_2$) unless otherwise noted. The current was measured using in-house built GeniaChip™ DNA sequencers.

Channel current traces of OmpG-ΔL6/E229A-Y50K (SEQ ID NO:6), OmpG-ΔL6/E229A-R68N (SEQ ID NO:7), OmpG-ΔL6/E229A-R211N (SEQ ID NO:8), OmpG-ΔL6/E229A-E17K (SEQ ID NO:9), and OmpG-ΔL6/E229A-del215 (SEQ ID NO:10) are shown in FIGS. 4A-4E. The traces show that OmpG-ΔL6/E229A-R68N (B), OmpG-ΔL6/E229A-R211N (C), OmpG-ΔL6/E229A-E17K (D), display substantial flickering, i.e., upward and downward currents. OmpG-ΔL6/E229A-Y50K (A) displays less flickering, and a lower open channel current level of about 30 pA. OmpG-ΔL6/E229A-del215 (E) shows the least level of spontaneous gating, and maintains an open channel level of about 35 pA.

Figure 5A:
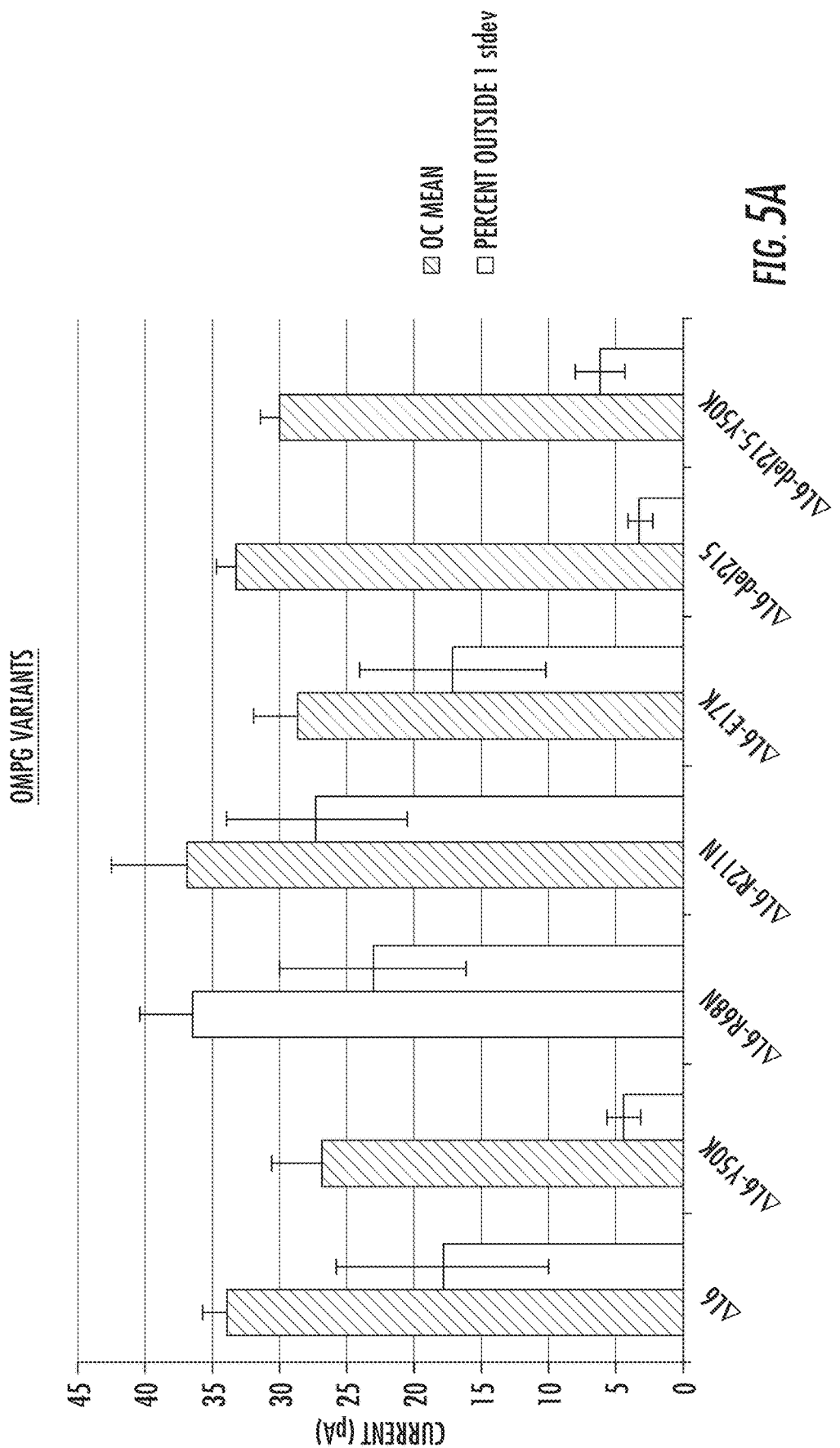
FIGS. 5A-5B depict the mean open channel (OC) current (filled bar) and the percentage of events greater than 1 standard deviation of the mean open channel in both higher and lower directions (FIG. 5A) and the mean open channel current in black (filled bar) and the percentage of events greater than 1 std deviation of the mean open channel in only the lower direction (downward current only) (FIG. 5B) determined for each of the OmpG variants of ΔL6/E229A (SEQ ID NO:5), and the amino acid substitution ΔL6/E229A-Y50K (SEQ ID NO:6), ΔL6/E229A-R68N (SEQ ID NO:7), ΔL6/E229A-R211N (SEQ ID NO:8), ΔL6/E229A-E17K (SEQ ID NO:9), and the amino acid deletion ΔL6/E229A-del215 (SEQ ID NO:10); (de1215)); ΔL6/E229A-del215-Y50K (SEQ ID NO:11).

The number of resistive events measured for the OmpG-ΔL6/E229A variants and for variant OmpG-ΔL6/E229A-del215-Y50K (FIGS. 4A-4E) was analyzed to calculate the effect of the mutations on gating frequency. FIG. 5A shows a histogram that relates the mean and S.D. of the open channel (OC) current noise (upward and downward current) to the percent of the same measurements that occurred outside 1 S.D. from the mean measurements. The histogram shows that OmpG-ΔL6/E229A-del215 (del215) ("ΔL6-del215" in FIGS. 5A and 5B) has the lowest amount of noise when compared to the parental OmpG-ΔL6/E229A ("ΔL6" in FIGS. 5A and 5B), and to other variants: OmpG-ΔL6/E229A-Y50K ("ΔL6-Y50K" in FIGS. 5A and 5B), OmpG-ΔL6/E229A-R68N ("ΔL6-R68N" in FIGS. 5A and 5B), OmpG-ΔL6/E229A-R211N ("ΔL6-R211N" in FIGS. 5A and 5B), OmpG-ΔL6/E229A-E17K ("ΔL6-E17K" in FIGS. 5A and 5B), and OmpG-ΔL6/E229A-del215-Y50K ("ΔL6-Y50K" in FIGS. 5A and 5B), and maintains an open channel current of about 35 pA.

Figure 5B:
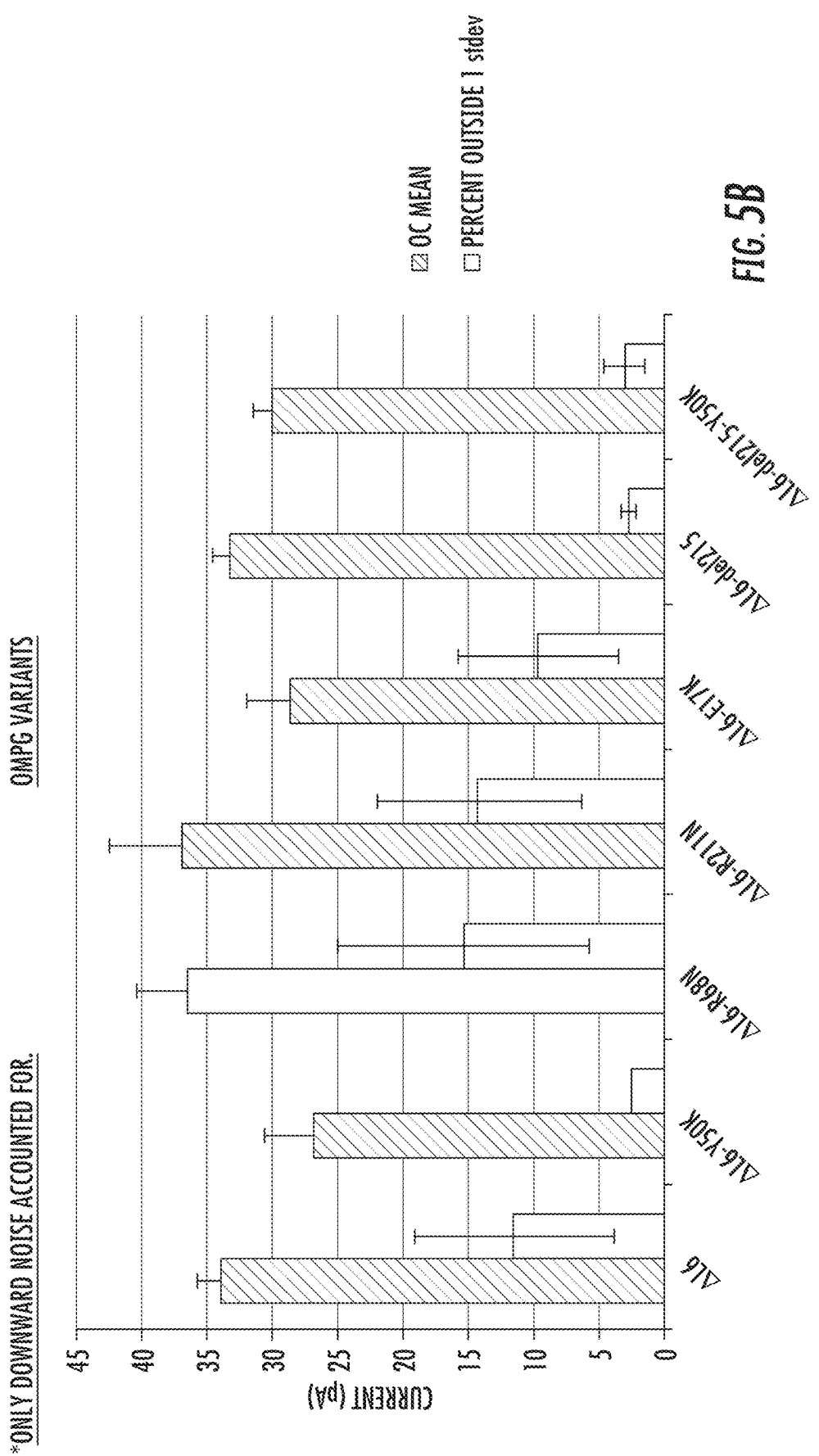

The mean and S.D. of the downward current only is provided in FIG. 5B. The OmpG-ΔL6/E229A-Y50K, OmpG-ΔL6/E229A-del215, and OmpG-ΔL6/E229A-del215-Y50K showed the smallest amount of downward current when compared, for example, to the parental OmpG-ΔL6/E229A.

Example 3

Attachment of a Polymerase to an OmpG Nanopore

A DNA sequence that encodes a His-tagged polymerase, pol6, was purchased from a commercial source (DNA 2.0, Menlo Park, California), and then engineered to comprise a SpyCatcher domain at its C-terminus. (Li et al., *J Mol Biol* 23:426(2):309-317 [2014]). The Pol6 was ligated into the pD441 vector (expression plasmid), which was subsequently transformed into competent *E. coli*. 1 ml starter culture in LB with 0.2% Glucose and 100 µg/ml Kanamycin for approximately 8 hrs. 25 µl of log phase starter culture was transferred into 1 ml of expression media (Terrific Broth (TB) autoinduction media supplemented with 0.2% glucose, 50 mM Potassium Phosphate, 5 mM MgCl2 and 100 µg/ml Kanamycin) in 96-deep well plates. The plates were incubated with shaking at 250-300 rpm for 36-40 hrs at 28° C.

Cells were then harvested via centrifugation at 3200×g for 30 minutes at 4° C. The media was decanted off and the cell pellet resuspended in 200 µl pre-chilled lysis buffer (20 mM Potassium Phosphate pH 7.5, 100 mM NaCl, 0.5% Tween20, 5 mM TCEP, 10 mM Imidazole, 1 mM PMSF, 1X BugBuster® protein extraction reagent, 100 µg/ml Lysozyme and protease inhibitors) and incubate at room temperature for 20 min with mild agitation. 20 µl of reagent was then added from a 10×stock to a final concentration of 100 µg/ml DNase, 5 mM MgCl2, 100 µg/ml RNase I, and incubated on ice for 5-10 min to produce a lysate. The lysate was supplemented with 200 µl of 1M Potassium Phosphate, pH 7.5 (final concentration was about 0.5M Potassium phosphate in 400 µl lysate) and filtered through Pall filter plates (Part #5053, 3 micron filters) via centrifugation at approximately 1500 rpm at 4° C. for 10 minutes. The clarified lysates were then applied to equilibrated 96-well His-Pur Cobalt plates (Pierce Part #90095) and bound for 15-30 min.

The flow through (FT) was collected by centrifugation at 500×g for 3 min. The FT was then washed 3 times with 400 µl of wash buffer 1 (0.5M Potassium Phosphate pH 7.5, 1M NaCl 5 mM TCEP, 20 mM Imidazole, and 0.5% Tween20). The FT was then washed twice in 400 µl wash buffer 2 (50 mM Tris pH 7.4, 200 mM KCl, 5 mM TCEP, 0.5% Tween20, 20 mM Imidazole). The Pol6 was eluted using 200 µl elution buffer (50 mM Tris Ph7.4, 200 mM KCl, 5 mM TCEP, 0.5% Tween20, 300 mM Imidazole, 25% Glycerol) and collected after 1-2 min incubation. Eluate was reapplied to the same His-Pur plate 2-3 times to obtain concentrated Pol6. The purified polymerase was >95% pure as evaluated by SDS-PAGE. The protein concentration was ~3 uM (0.35 mg/ml) with a 260/280 ratio of 0.6 as evaluated by NanoDrop®. Polymerase activity was checked by fluorescence displacement assay.

The Pol6-His-SpyCatcher protein was incubated overnight at 4° C. in 3 mM SrCl$_2$ with the OmpG-EXT-His-SpyTag (SEQ ID NO:3) to allow for the covalent attachment of the SpyCatcher with the SpyTag, thereby forming an OmpG-polymerase complex. The OmpG-polymerase complex was purified using affinity chromatography, and tested for its ability to capture and identify tagged nucleotides as described in Example 4.

Example 4

Detection of Nucleotide Bases by Polymerase-Variant OmpG Complexes

The ability of OmpG-EXT-del1215 (SEQ ID NO:10), i.e., OmpG-ΔL6/E229A-del215, to identify nucleotides captured by a polymerase was assessed using OmpG-EXT-del215 complexed with polymerase Pol6 in the presence of DNA template JAM1A in 300 mM NaCl, 3 mM CaCl$_2$), 20 mM HEPES, pH 7.5. Template JAM1A is a DNA template that provides an adenine nucleotide base that is complementary to the tagged thymidine nucleotide used in the assay (Synthesized by Roche Penzberg, Germany) and that would be captured by the polymerase.

Figure 6:
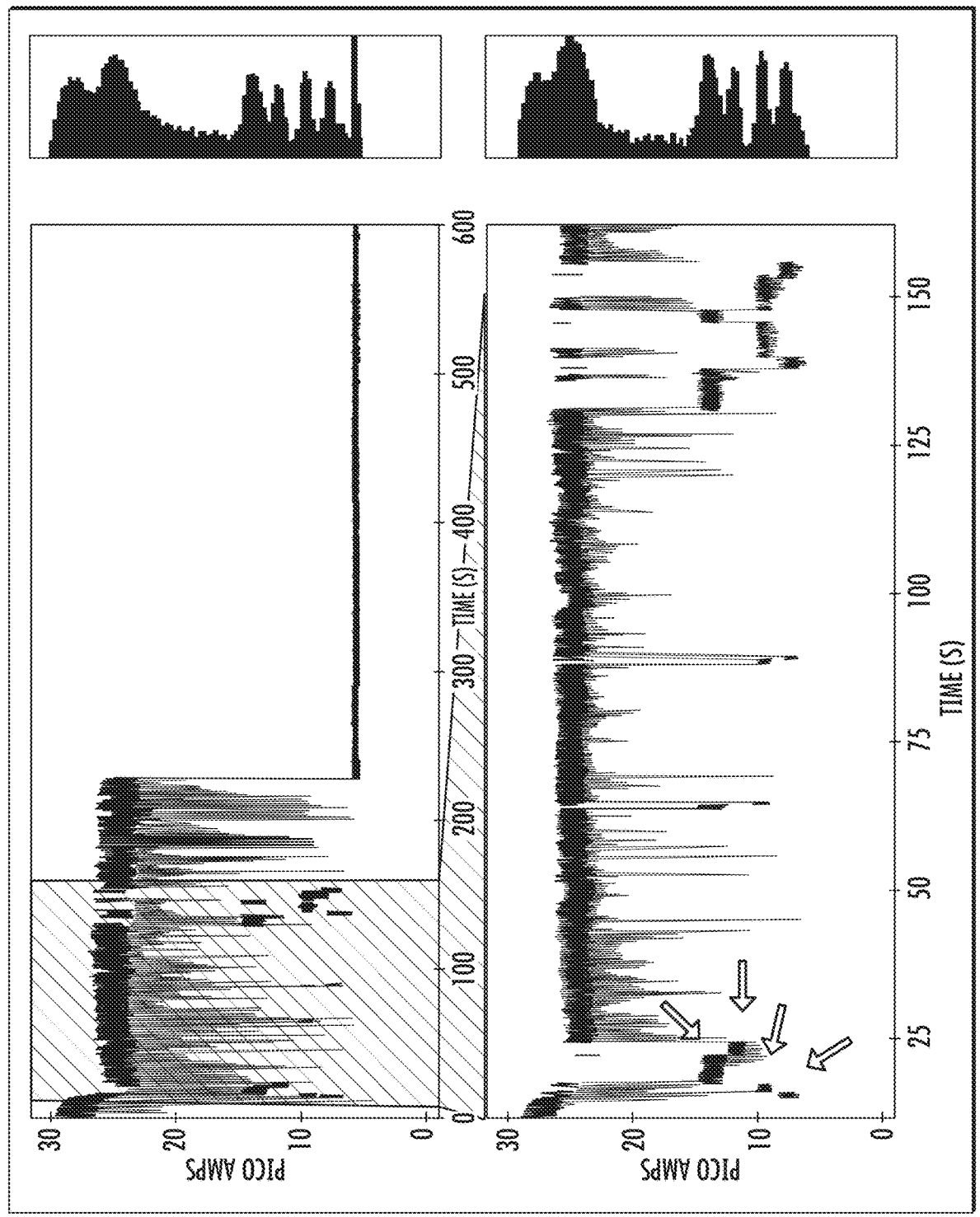
FIG. 6 depicts the single nucleotide resolution of a mixture of four different tagged nucleotides shown as changes in baseline open channel direct current (block arrows) as each of the tagged nucleotides is detected by the variant OmpG nanopore ΔL6/E229A-del215 (SEQ ID NO:10). Measurements were made with the application of a direct current (DC).
Figure 7A:
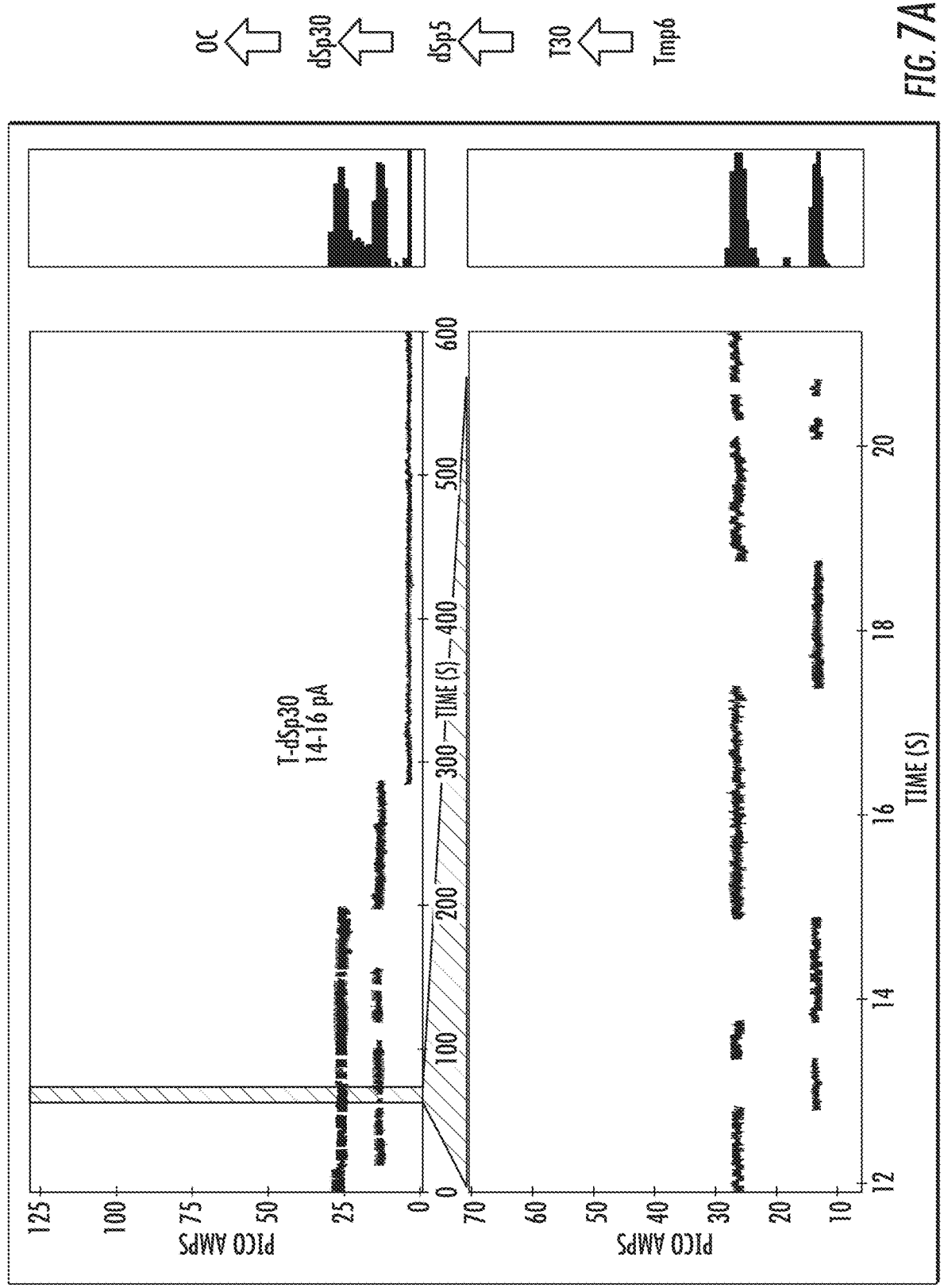
Figure 7B:
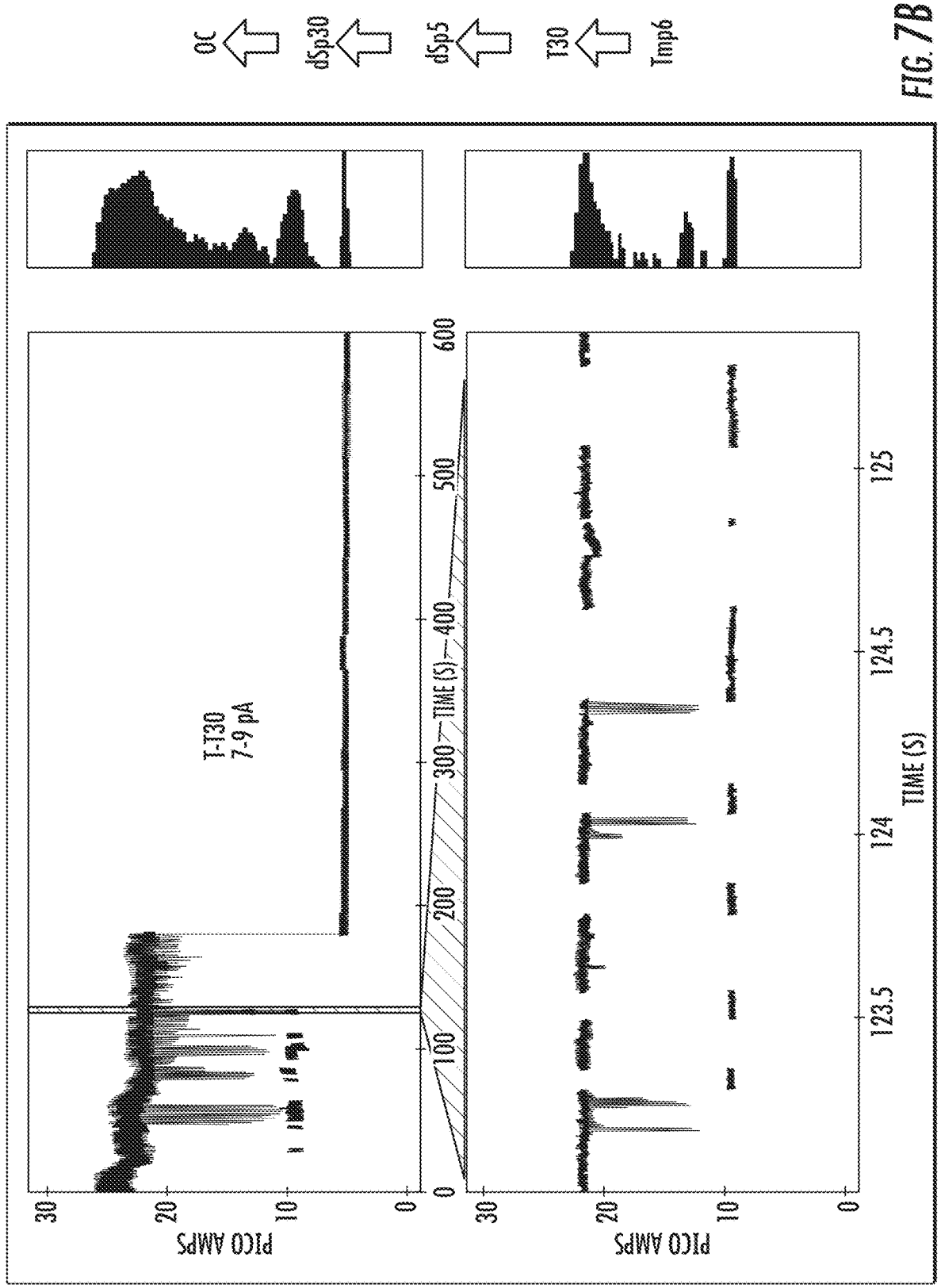
Figure 7C:
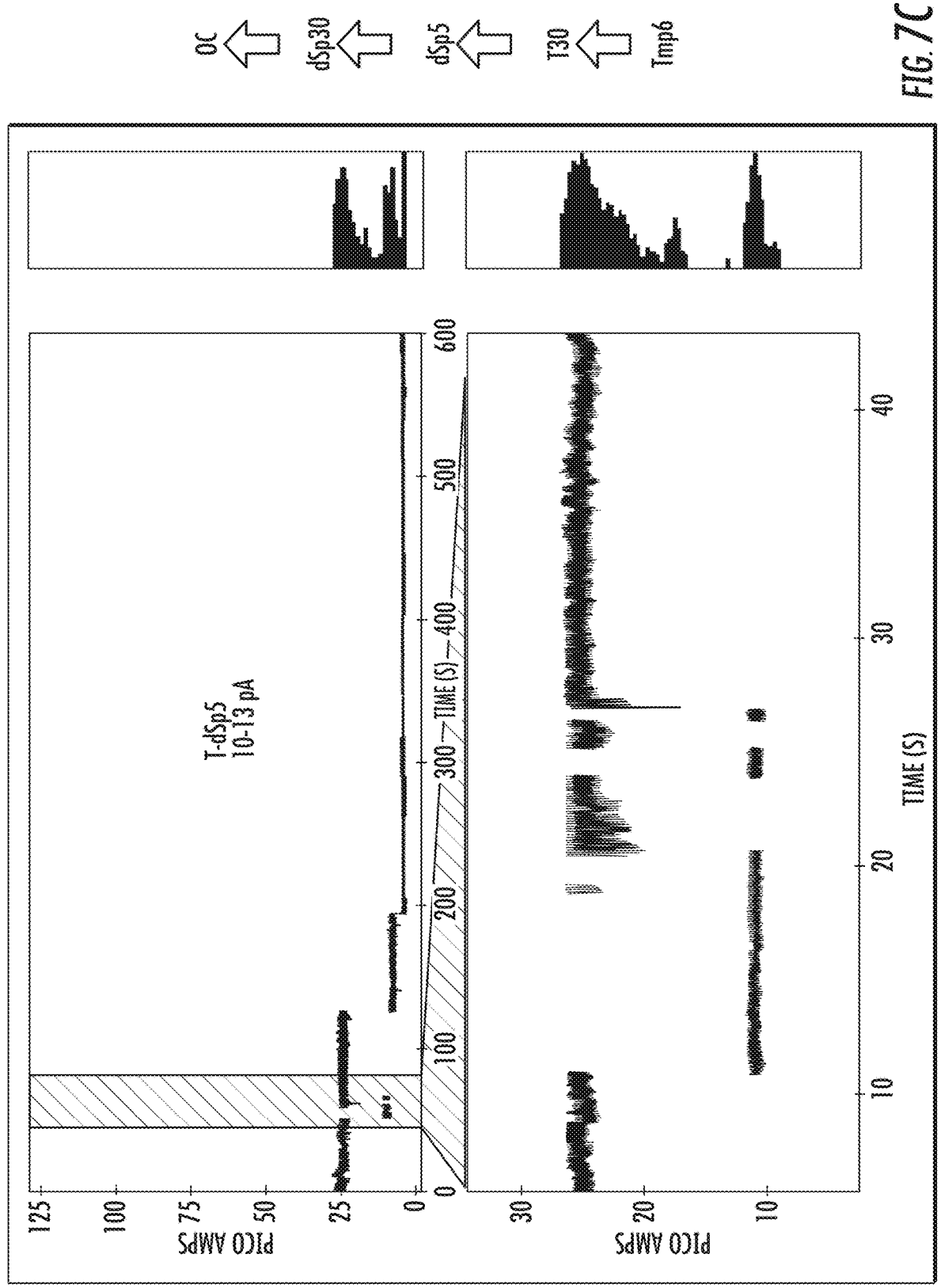
Figure 8:
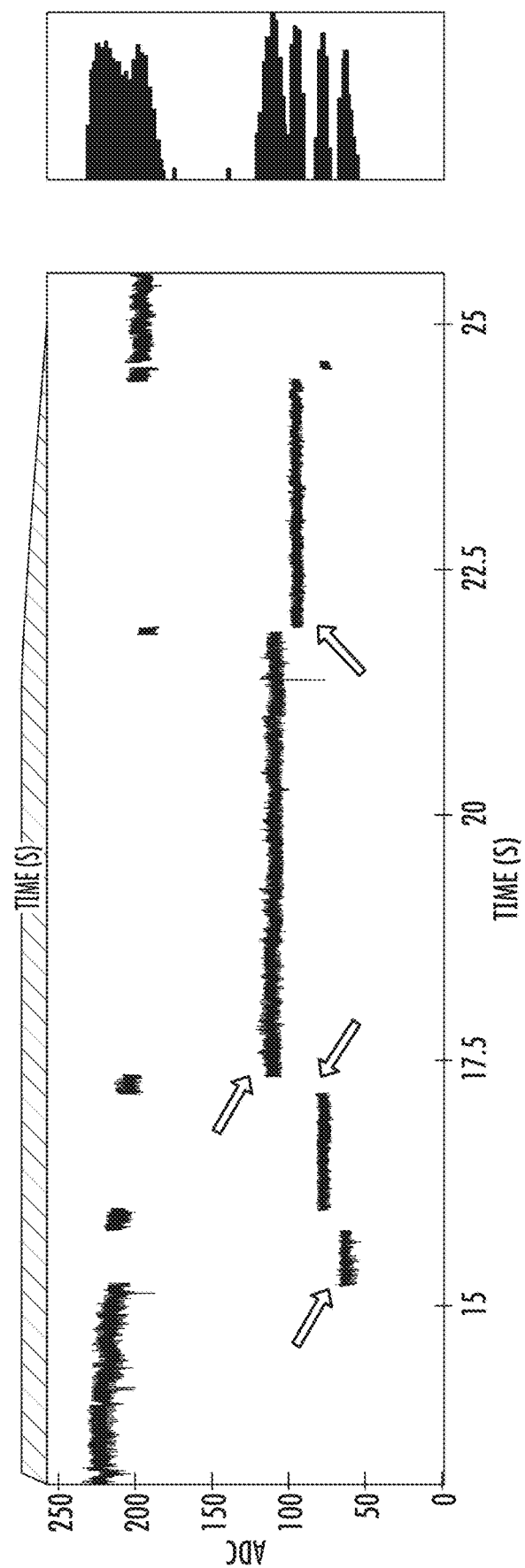
FIG. 8 depicts an expanded view of the single nucleotide resolution of the mixture of four different tagged nucleotides shown in FIG. 6 as detected by the variant OmpG nanopore ΔL6/E229A-del215 (SEQ ID NO:10) (block arrows). Measurements were made with the application of a direct current (DC).
Figure 9A:
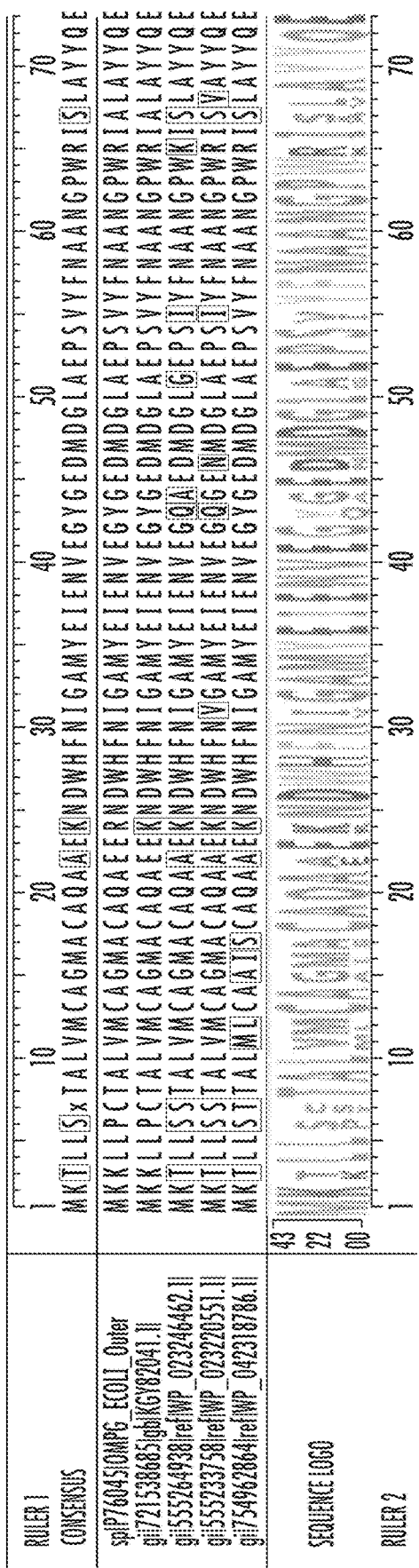
Figure 9B:
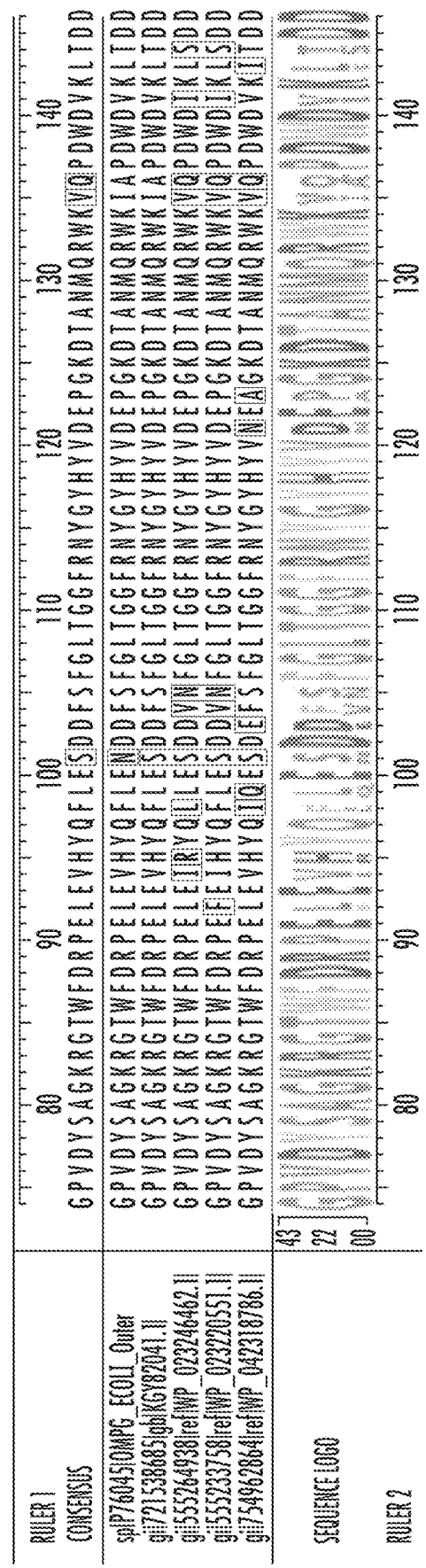
Figure 9C:
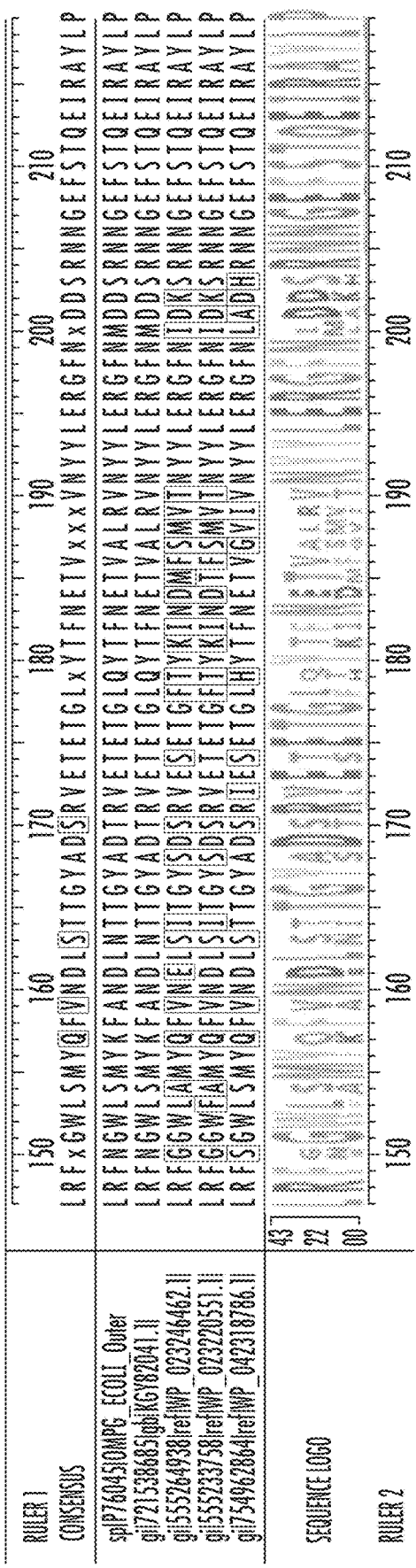
Figure 9D:
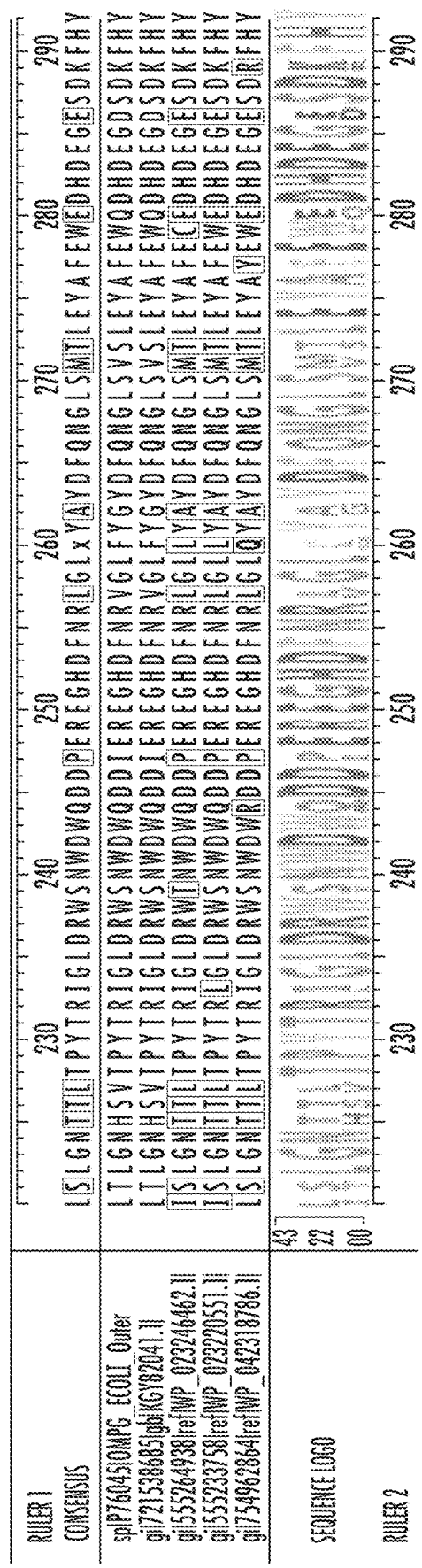

DC current measurements were made at a constant voltage of 100 mV applied for 10 minutes. Different sets of tagged nucleotides were used. FIG. 6 shows an example of a trace that demonstrates that the OmpG-EXT-del215—polymerase complex identifies four different tagged nucleotides that were captured by the polymerase: T-T30, T-dSp30, T-Tmp6, and T-dSp5. Capture of each of the four nucleotides is reflected by four different changes in the current flowing thorough OmpG-EXT-del215 nanopore as the corresponding nucleotide tags are detected by the nanopore (FIG. 6). The arrows indicate the four tags of the tagged nucleotides diminish channel current to four different levels. Each of the four nucleotides were identified in similar measurements during which current was measured as the nucleotides were individually added to the nanopore. FIG. 7 shows the identification of the nucleotides by the individual effects of the corresponding tags on reducing the open channel current as they were detected by the nanopore. FIG. 8 shows an expanded view of the capture of the four nucleotides detected under DC conditions and indicated by the arrows in FIG. 6.

```
                    SEQUENCE LISTING FREE TEXT

SEQ ID NO: 1 (Wild-type OmpG; >sp|P76045|OMPG_ECOLI Outer
membrane protein G; OS = Escherichia coli (strain K12))
MKKLLPCTAL VMCAGMACAQ AEERNDWHEN IGAMYEIENV EGYGEDMDGL        50
AEPSVYFNAA NGPWRIALAY YQEGPVDYSA GKRGTWEDRP ELEVHYQFLE       100
NDDFSFGLTG GFRNYGYHYV DEPGKDTANM QRWKIAPDWD VKLIDDLREN       150
GWLSMYKFAN DLNTTGYADT RVETETGLQY TENETVALRV NYYLERGENM       200
DDSRNNGEFS TQEIRAYLPL TLGNHSVTPY TRIGLDRWSN WDWQDDIERE       250
GHDFNRVGLF YGYDFQNGLS VSLEYAFEWQ DHDEGDSDKF HYAGVGVNYS       300
F SEQ ID NO: 2 (Mature wild-type OmpG from E.coli (strain K12);
sequence for numbering))
EERNDWHENI GAMYEIENVE GYGEDMDGLA EPSVYFNAAN GPWRIALAYY        50
QEGPVDYSAG KRGTWFDRPE LEVHYQFLEN DDFSFGLIGG FRNYGYHYVD       100
EPGKDTANMQ RWKIAPDWDV KLIDDLRENG WLSMYKFAND LNTTGYADTR       150
VETETGLQYT FNETVALRVN YYLERGENMD DSRNNGEFST QEIRAYLPLT       200
LGNHSVTPYT RIGLDRWSNW DWQDDIEREG HDFNRVGLFY GYDFQNGLSV       250
SLEYAFEWQD HDEGDSDKFH YAGVGVNYSF                            280
```

| SEQUENCE LISTING FREE TEXT |
|---|

SEQ ID NO: 3 (Synthetic OmpG-AL6 fusion protein-HisTag-SpyTag
as expressed in E.coli)
```
EERNDWHENI GAMYEIENVE GYGEDMDGLA EPSVYFNAAN GPWRIALAYY      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       299
```

SEQ ID NO: 4 (Wild-Type OmpG; Escheridia coli porin (ompG) gene GI:1806593)
```
atgaaaaagttattaccctgtaccgcactggtgatgtgtgcgggaatggcctgcgcacaggccgaggaaaggaac
gactggcactttaatatcggcgatgtacgaaatagaaaacgttgagtgcgaagatattggatgggctg
gcggagccttcagtctattttaatgccgccaacgggccgtggagaattgctctggcctattatcaggaagggccg
gtagattatagcgcgggtaaacgtggaacgtggtttgatcgcccggagctggaggtgcattatcagttcctcgaa
aacgatgatttcagtttcggcctgaccggcggtttccgtaattatggttatcactacgttgatgaaccgggtaaa
gacacggcgaatatgactgctgggaaaatcgcgccagactgggatgtgaaacttacgtttcaac
ggttggttgtcgatgtataaatttgccaacgatctgaacactaccggttacgctgatacccgtgtcgaaacggaa
acaggtctgcaatataccttcaacgaaacggttgccttgcgagtgaactattatctcgagcgcggcttcaatatg
gacgacagccgcaataacggtgagttttccacgcaagaaattcgcgcctatttgccgctgacgctcggcaaccac
tcggtgacgccgtatacgcgcattgggctggatcgctgagtaactggcaggatgatattgaacgtgaa
ggccatgattttaaccgtgtaggtttattttacggttatgatttccagaacggactttccgtttcgctggaatac
gcgtttgagtggcaggatcacgacgaaggcgacagtgataaattccattatgcaggtgtcggcgtaaattactcg
ttctgataat
```

SEQ ID NO: 5 (OmpG-ΔL6)
```
EERNDWHENI GAMYEIENVE GYGEDMDGLA EPSVYFNAAN GPWRIALAYY      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       268
```

SEQ ID NO: 6 (Ompg-ΔL6-Y50K)
```
EERNDWHENI GAMYEIENVE GYGEDMDGLA EPSVYFNAAN GPWRIALAYK      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       299
```

SEQ ID NO: 7 (ΔL6-R68N OmpG)
```
EERNDWHENI GAMYEIENVE GYGEDMDGLA EPSVYFNAAN GPWRIALAYY      50
QEGPVDYSAG KRGTWEDNPE LEVHYQFLEN DDFSEGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       299
```

SEQ ID NO: 8 (ΔL6-R211N OmpG)
```
EERNDWHENI GAMYEIENVE GYGEDMDGLA EPSVYFNAAN GPWRIALAYY      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT NIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       299
```

SEQ ID NO: 9 (ΔL6-E17K OmpG)
```
EERNDWHENI GAMYEIKNVE GYGEDMDGLA EPSVYFNAAN GPWRIALAYY      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLDRAGHD FNRVGLFYGY DFQNGLSVSL EYAFEWQDHD     250
EGDSDKFHYA GVGVNYSFEK EKEKGSHHHH HGSGGAHIV MVDAYKPTK       299
```

SEQ ID NO: 10 (ΔL6-del215 OmpG)
```
EERNDWHENI GAMYEIENVE GYGEDMDGLA EPSVYFNAAN GPWRIALAYY      50
QEGPVDYSAG KRGTWFDRPE LEVHYQFLEN DDFSFGLIGG FRNYGYHYVD     100
EPGKDTANMQ RWKIAPDWDV KLIDDLRENG WLSMYKFAND LNTTGYADTR     150
VETETGLQYT FNETVALRVN YYLERGENMD DSRNNGEFST QEIRAYLPLT     200
LGNHSVTPYT RIGLRAGHDF NRVGLFYGYD FQNGLSVSLE YAFEWQDHDE     250
GDSDKFHYAG VGVNYSFEKE KEKGSHHHHH HGSGGAHIVM VDAYKPTK       298
```

SEQ ID NO: 11 (ΔL6-del215-Y50K OmpG)
```
EERNDWHENI GAMYEIENVE GYGEDMDGLA EPSVYFNAAN GPWRIALAYK      50
QEGPVDYSAG KRGTWFDRPE LEVHYQFLEN DDFSFGLIGG FRNYGYHYVD     100
EPGKDTANMQ RWKIAPDWDV KLTDDLRENG WLSMYKFAND LNTTGYADTR     150
VETETGLQYT FNETVALRVN YYLERGENMD DSRNNGEFST QEIRAYLPLT     200
```

-continued

SEQUENCE LISTING FREE TEXT

```
LGNHSVTPYT RIGLRAGHDF NRVGLFYGYD FQNGLSVSLE YAFEWQDHDE    250
GDSDKFHYAG VGVNYSFEKE KEKGSHHHHH HGSGGAHIVM VDAYKPTK      298

SEQ ID NO: 12 (membrane protein (Shigella flexneri); KGY82041)
MKKLLPCTAL VMCAGMACAQ AEEKNDWHEN IGAMYEIENV EGYGEDMDGL     50
AEPSVYFNAA NGPWRIALAY YQEGPVDYSA GKRGTWFDRP ELEVHYQFLE    100
SDDFSFGLTG GFRNYGYHYV DEPGKDTANM QRWKIAPDWD VKLTDDLREN    150
GWLSMYKFAN DLNTTGYADT RVETETGLQY TENETVALRV NYYLERGENM    200
DDSRNNGEFS TQEIRAYLPL TLGNHSVTPY TRIGLDRWSN WDWQDDIERE    250
GHDFNRVGLF YGYDFQNGLS VSLEYAFEWQ DHDEGDSDKF HYAGVGVNYS    300
F                                                         301

SEQ ID NO: 13 (outer membrane protein G (Salmonella enterica); WP_023246462)
MKTLLSSTAL VMCAGMACAQ AAEKNDWHFN IGAMYEIENV EGQAEDMDGL     50
GEPSIYFNAA NGPWKISLAY YQEGPVDYSA GKRGTWEDRP ELEIRYQLLE    100
SDDVNFGLIG GFRNYGYHYV DEPGKDTANM QRWKVQPDWD IKLSDDLRFG    150
GWLAMYQFVN ELSITGYSDS RVESETGFTY KINDMFSMVT NYYLERGENI    200
DKSRNNGEFS TQEIRAYLPI SLGNTTLTPY TRIGLDRWTN WDWQDDPERE    250
GHDFNRLGLL YAYDFQNGLS MTLEYAFECE DHDEGESDKF HYAGIGINYA    300
F                                                         301

SEQ ID NO: 14 (outer membrane protein G (Salmonella enterica); WP_023220551)
MKTLLSSTAL VMCAGMACAQ AAEKNDWHFN VGAMYEIENV EGQGENMDGL     50
AEPSIYFNAA NGPWRISVAY YQEGPVDYSA GKRGTWFDRP EFEVHYQFLE    100
SDDVNFGLIG GFRNYGYHYV DEPGKDTANM QRWKVQPDWD IKLSDDLRFG    150
GWFAMYQFVN DLSITGYSDS RVETETGFTY KINDTFSMVT NYYLERGENI    200
DKSRNNGEFS TQEIRAYLPI SLGNTTLTPY TRLGLDRWSN WDWQDDPERE    250
GHDFNRLGLL YAYDFQNGLS MTLEYAFEWE DHDEGESDKF HYAGVGINYA    300

SEQ ID NO: 15 (membrane protein (Citrobacter farmeri); WP_042318786)
MKTLLSTTAL MLCAAISCAQ AAEKNDWHFN IGAMYEIENV EGYGEDMDGL     50
AEPSVYFNAA NGPWRISLAY YQEGPVDYSA GKRGTWEDRP ELEVHYQIQE    100
SDEFSFGLTG GFRNYGYHYV NEAGKDTANM QRWKVQPDWD VKITDDLRES    150
GWLSMYQFVN DLSTTGYADS RLESETGLHY TENETVGVIV NYYLERGENL    200
ADHRNNGEFS TQEIRAYLPL SIGNTTLTPY TRIGLDRWSN WDWRDDPERE    250
GHDFNRLGLQ YAYDFQNGLS MTLEYAYEWE DHDEGESDRF HYAGVGVNYA    300
F                                                         301

SEQ ID NO: 16 ((EK)3-His6-GSGG-SpyTag-linker-HisSpyTag construct)
EKEKEKGSHH HHHHGSGGAH IVMVDAYKPT K                         31

SEQ ID NO: 17 Circular permutation variant of E. coli OmpG
MDKFHYAGVGVNYSFGSGEERNDWHENIGAMYEIENVEGYGEDMDGLAEPSVYFNAANGPWRIALAYKQEGPVDY
SAGKRGTWFDRPELEVHYQFLENDDFSFGLTGGFRNYGYHYVDEPGKDTANMQRWKIAPDWDVKLIDDLRENGWL
SMYKFANDLNTTGYADTRVETETGLQYTFNETVALRVNYYLERGENMDDSRNNGEFSTQEIRAYLPLTLGNHSVT
PYTRIGLRAGHDFNRVGLFYGYDFQNGLSVSLEYAFEWQDHDEGDSEKEKEKGSHHHHHHGSGGAHIVMVDAYKP
TK
```

CITATION LIST

Patent Literature

PCT/US2005/009702 (published as WO2006/028508 on 16 Mar. 2006; President and Fellows of Harvard College; entitled METHODS AND APPARATUS FOR CHARACTERIZING POLYNUCLEOTIDES.

PCT/US2011/065640 (published as WO2012/083249 on 21 Jun. 2012; Columbia University; entitled DNA SEQUENCING BY SYNTHESIS USING MODIFIED NUCLEOTIDES AND NANOPORE DETECTION).

PCT/US2013/068967 (published as WO2014/074727 on 15 May 2014; Genia Technologies; entitled NUCLEIC ACID SEQUENCING USING TAGS).

US20140134616 (published on May 15, 2014; Genia Technologies; entitled NUCLEIC ACID SEQUENCING USING TAGS).

PCT/US2014/061853 (published AS WO2015/061510 on Apr. 30, 2015; Genia Technologies; entitled METHODS FOR FORMING LIPID BILAYERS ON BIOCHIPS).

PCT/US2011/000205 (Genia Technologies, Inc. entitled SYSTEMS FOR MANIPULATING A MOLECULE IN A NANOPORE, published Aug. 11, 2011 as WO2011/097028)

Non-Patent Literature

Conlan and Bayley, Folding of a Monomeric Porin, OmpG, in *Detergent Solution*; Biochemistry 42; 9453-9465 (2003).

Subbarao and van den Berg, Crystal Structure of the monomeric Porin OmpG; *J Mol Biol* 360:750-759 (2006).

Grosse et al., Structural and functional characterization of a synthetically modified OmpG; *Bioorganic and Medicinal Chem* 18:7716-7723 (2010).

Anbazhagan et al., Incorporation of Outer Membrane Protein OmpG in Lipid Membranes: Protein-lipid Interactions and β-Barrel Orientation; *Biochemistry* 47:6189-698 (2008).

Fahie et al., Resolved Single-Molecule Detection of Individual Species within a Mixture of anti-Biotin Antibodies using an Engineered Monomeric Nanopore; *ACS Nano* 9:1089-1098 (2015).

Chen et al., Outer membrane protein G: Engineering a quiet pore for biosensing, *Proc Natl Acad Sci* 105:6272-6277 (2008).

Grosse et al., Structure-based Engineering of a Minimal Porin Reveals Loop-Independent Channel closure; *Biochemistry* 53:4826-4838 (2014).

Astier et al., *J Am Chem Soc* 10.1021/ja057123+, published online on Dec. 30, 2005.

```
                              SEQUENCE LISTING

Sequence total quantity: 23
SEQ ID NO: 1            moltype = AA  length = 301
FEATURE                 Location/Qualifiers
source                  1..301
                        mol_type = protein
                        organism = Escherichia coli
SEQUENCE: 1
MKKLLPCTAL VMCAGMACAQ AEERNDWHFN IGAMYEIENV EGYGEDMDGL AEPSVYFNAA  60
NGPWRIALAY YQEGPVDYSA GKRGTWFDRP ELEVHYQFLE NDDFSFGLTG GFRNYGYHYV 120
DEPGKDTANM QRWKIAPDWD VKLTDDLRFN GWLSMYKFAN DLNTTGYADT RVETETGLQY 180
TFNETVALRV NYYLERGFNM DDSRNNGEFS TQEIRAYLPL TLGNHSVTPY TRIGLDRWSN 240
WDWQDDIERE GHDFNRVGLF YGYDFQNGLS VSLEYAFEWQ DHDEGDSDKF HYAGVGVNYS 300
F                                                                301

SEQ ID NO: 2            moltype = AA  length = 280
FEATURE                 Location/Qualifiers
source                  1..280
                        mol_type = protein
                        organism = Escherichia coli
SEQUENCE: 2
EERNDWHFNI GAMYEIENVE GYGEDMDGLA EPSVYFNAAN GPWRIALAYY QEGPVDYSAG  60
KRGTWFDRPE LEVHYQFLEN DDFSFGLTGG FRNYGYHYVD EPGKDTANMQ RWKIAPDWDV 120
KLTDDLRFNG WLSMYKFAND LNTTGYADTR VETETGLQYT FNETVALRVN YYLERGFNMD 180
DSRNNGEFST QEIRAYLPLT LGNHSVTPYT RIGLDRWSNW DWQDDIEREG HDFNRVGLFY 240
GYDFQNGLSV SLEYAFEWQD HDEGDSDKFH YAGVGVNYSF                       280

SEQ ID NO: 3            moltype = AA  length = 299
FEATURE                 Location/Qualifiers
REGION                  1..299
                        note = Description of Artificial Sequence: Synthetic
                        polypeptide
source                  1..299
                        mol_type = protein
                        organism = synthetic construct
SEQUENCE: 3
EERNDWHFNI GAMYEIENVE GYGEDMDGLA EPSVYFNAAN GPWRIALAYY QEGPVDYSAG  60
KRGTWFDRPE LEVHYQFLEN DDFSFGLTGG FRNYGYHYVD EPGKDTANMQ RWKIAPDWDV 120
KLTDDLRFNG WLSMYKFAND LNTTGYADTR VETETGLQYT FNETVALRVN YYLERGFNMD 180
DSRNNGEFST QEIRAYLPLT LGNHSVTPYT RIGLDRAGHD FNRVGLFYGY DFQNGLSVSL 240
EYAFEWQDHD EGDSDKFHYA GVGVNYSFEK EKEKGSHHHH HHGSGGAHIV MVDAYKPTK  299

SEQ ID NO: 4            moltype = DNA  length = 910
FEATURE                 Location/Qualifiers
source                  1..910
                        mol_type = genomic DNA
                        organism = Escherichia coli
SEQUENCE: 4
atgaaaaagt tattaccctg taccgcactg gtgatgtgtg cgggaatggc ctgcgcacag  60
gccgaggaaa ggaacgactg gcactttaat atcggcgcga tgtacgaaat agaaaacgtc 120
gagggttatg gcgaagatat ggatgggctg gcggagcctt cagtctattt taatgccgcc 180
aacgggccgt ggagaattgc tctggcctat tatcaggaag gccggtaga ttatagcgcg  240
ggtaaacgtg gaacgtggtt tgatcgcccg gagctggagg tgcattatca gttcctcgaa 300
aacgatgatt tcagtttcgg cctgaccggc ggtttccgta attatggtta tcactacgtt 360
gatgaaccgg gtaaagacac ggcgaatatg cagcgctgga aaatcgcgcc agactgggat 420
gtgaaactga ctgacgattt acgtttcaac ggttggttgt cgatgtataa atttgccaac 480
gatctgaaca ctaccggtta cgctgatacc cgtgtcgaaa cggaaacagg tctgcaatat 540
accttcaacg aaacggttgc cttgcgagtg aactattatc tcgagcgcgg cttcaatatg 600
gacgacagcc gcaataacgg tgagttttcc acgcaagaaa ttcgcgccta tttgccgctg 660
acgctcggca accactcggt gacgccgtat acgcgcattg gctggatcg ctggagtaac  720
tgggactggc aggatgatat tgaacgtgaa ggccatgatt ttaaccgtgt aggttatttt 780
tacggttatg atttccagaa cggactttcc gtttcgctgg aatacgcgtt tgagtggcag 840
gatcacgacg aaggcgacag tgataaattc cattatgcag gtgtcggcgt aaattactcg 900
ttctgataat                                                       910

SEQ ID NO: 5            moltype = AA  length = 299
FEATURE                 Location/Qualifiers
REGION                  1..299
```

-continued

```
                        note = Description of Artificial Sequence: Synthetic
                             polypeptide
source                  1..299
                        mol_type = protein
                        organism = synthetic construct
SEQUENCE: 5
EERNDWHFNI GAMYEIENVE GYGEDMDGLA EPSVYFNAAN GPWRIALAYY QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLDRAGHD FNRVGLFYGY DFQNGLSVSL   240
EYAFEWQDHD EGDSDKFHYA GVGVNYSFEK EKEKGSHHHH HHGSGGAHIV MVDAYKPTK    299

SEQ ID NO: 6            moltype = AA  length = 299
FEATURE                 Location/Qualifiers
REGION                  1..299
                        note = Description of Artificial Sequence: Synthetic
                             polypeptide
source                  1..299
                        mol_type = protein
                        organism = synthetic construct
SEQUENCE: 6
EERNDWHFNI GAMYEIENVE GYGEDMDGLA EPSVYFNAAN GPWRIALAYK QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLDRAGHD FNRVGLFYGY DFQNGLSVSL   240
EYAFEWQDHD EGDSDKFHYA GVGVNYSFEK EKEKGSHHHH HHGSGGAHIV MVDAYKPTK    299

SEQ ID NO: 7            moltype = AA  length = 299
FEATURE                 Location/Qualifiers
REGION                  1..299
                        note = Description of Artificial Sequence: Synthetic
                             polypeptide
source                  1..299
                        mol_type = protein
                        organism = synthetic construct
SEQUENCE: 7
EERNDWHFNI GAMYEIENVE GYGEDMDGLA EPSVYFNAAN GPWRIALAYY QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLDRAGHD FNRVGLFYGY DFQNGLSVSL   240
EYAFEWQDHD EGDSDKFHYA GVGVNYSFEK EKEKGSHHHH HHGSGGAHIV MVDAYKPTK    299

SEQ ID NO: 8            moltype = AA  length = 299
FEATURE                 Location/Qualifiers
REGION                  1..299
                        note = Description of Artificial Sequence: Synthetic
                             polypeptide
source                  1..299
                        mol_type = protein
                        organism = synthetic construct
SEQUENCE: 8
EERNDWHFNI GAMYEIENVE GYGEDMDGLA EPSVYFNAAN GPWRIALAYY QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT NIGLDRAGHD FNRVGLFYGY DFQNGLSVSL   240
EYAFEWQDHD EGDSDKFHYA GVGVNYSFEK EKEKGSHHHH HHGSGGAHIV MVDAYKPTK    299

SEQ ID NO: 9            moltype = AA  length = 299
FEATURE                 Location/Qualifiers
REGION                  1..299
                        note = Description of Artificial Sequence: Synthetic
                             polypeptide
source                  1..299
                        mol_type = protein
                        organism = synthetic construct
SEQUENCE: 9
EERNDWHFNI GAMYEIKNVE GYGEDMDGLA EPSVYFNAAN GPWRIALAYY QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLDRAGHD FNRVGLFYGY DFQNGLSVSL   240
EYAFEWQDHD EGDSDKFHYA GVGVNYSFEK EKEKGSHHHH HHGSGGAHIV MVDAYKPTK    299

SEQ ID NO: 10           moltype = AA  length = 298
FEATURE                 Location/Qualifiers
REGION                  1..298
                        note = Description of Artificial Sequence: Synthetic
                             polypeptide
source                  1..298
                        mol_type = protein
```

```
                            organism = synthetic construct
SEQUENCE: 10
EERNDWHFNI GAMYEIENVE GYGEDMDGLA EPSVYFNAAN GPWRIALAYY QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLRAGHDF NRVGLFYGYD FQNGLSVSLE   240
YAFEWQDHDE GDSDKFHYAG VGVNYSFEKE KEKGSHHHHH HGSGGAHIVM VDAYKPTK     298

SEQ ID NO: 11           moltype = AA  length = 298
FEATURE                 Location/Qualifiers
REGION                  1..298
                        note = Description of Artificial Sequence: Synthetic
                         polypeptide
source                  1..298
                        mol_type = protein
                        organism = synthetic construct
SEQUENCE: 11
EERNDWHFNI GAMYEIENVE GYGEDMDGLA EPSVYFNAAN GPWRIALAYK QEGPVDYSAG    60
KRGTWFDRPE LEVHYQFLEN DDFSFGLTGG FRNYGYHYVD EPGKDTANMQ RWKIAPDWDV   120
KLTDDLRFNG WLSMYKFAND LNTTGYADTR VETETGLQYT FNETVALRVN YYLERGFNMD   180
DSRNNGEFST QEIRAYLPLT LGNHSVTPYT RIGLRAGHDF NRVGLFYGYD FQNGLSVSLE   240
YAFEWQDHDE GDSDKFHYAG VGVNYSFEKE KEKGSHHHHH HGSGGAHIVM VDAYKPTK     298

SEQ ID NO: 12           moltype = AA  length = 301
FEATURE                 Location/Qualifiers
source                  1..301
                        mol_type = protein
                        organism = Shigella flexneri
SEQUENCE: 12
MKKLLPCTAL VMCAGMACAQ AEEKNDWHFN IGAMYEIENV EGYGEDMDGL AEPSVYFNAA    60
NGPWRIALAY YQEGPVDYSA GKRGTWFDRP ELEVHYQFLE SDDFSFGLTG GFRNYGYHYV   120
DEPGKDTANM QRWKIAPDWD VKLTDDLRFN GWLSMYKFAN DLNTTGYADT RVETETGLQY   180
TFNETVALRV NYYLERGFNM DDSRNNGEFS TQEIRAYLPL TLGNHSVTPY TRIGLDRWSN   240
WDWQDDIERE GHDFNRVGLF YGYDFQNGLS VSLEYAFEWQ DHDEGSDKF  HYAGVGVNYS   300
F                                                                  301

SEQ ID NO: 13           moltype = AA  length = 301
FEATURE                 Location/Qualifiers
source                  1..301
                        mol_type = protein
                        organism = Salmonella enterica
SEQUENCE: 13
MKTLLSSTAL VMCAGMACAQ AAEKNDWHFN IGAMYEIENV EGQAEDMDGL GEPSIYFNAA    60
NGPWKISLAY YQEGPVDYSA GKRGTWFDRP ELEIRYQLLE SDDVNFGLTG GFRNYGYHYV   120
DEPGKDTANM QRWKVQPDWD IKLSDDLRFG WLAMYQFVN  ELSITGYSDS RVESETGFTY   180
KINDMFSMVT NYYLERGFNI DKSRNNGEFS TQEIRAYLPI SLGNTTLTPY TRIGLDRWTN   240
WDWQDDPERE GHDFNRLGLL YAYDFQNGLS MTLEYAFECE DHDEGESDKF HYAGIGINYA   300
F                                                                  301

SEQ ID NO: 14           moltype = AA  length = 301
FEATURE                 Location/Qualifiers
source                  1..301
                        mol_type = protein
                        organism = Salmonella enterica
SEQUENCE: 14
MKTLLSSTAL VMCAGMACAQ AAEKNDWHFN VGAMYEIENV EGQGENMDGL AEPSIYFNAA    60
NGPWRISVAY YQEGPVDYSA GKRGTWFDRP EFEVHYQFLE SDDVNFGLTG GFRNYGYHYV   120
DEPGKDTANM QRWKVQPDWD IKLSDDLRFG WFAMYQFVN  DLSITGYSDS RVETETGFTY   180
KINDTFSMVT NYYLERGFNI DKSRNNGEFS TQEIRAYLPI SLGNTTLTPY TRLGLDRWSN   240
WDWQDDPERE GHDFNRLGLL YAYDFQNGLS MTLEYAFEWE DHDEGESDKF HYAGVGINYA   300
F                                                                  301

SEQ ID NO: 15           moltype = AA  length = 301
FEATURE                 Location/Qualifiers
source                  1..301
                        mol_type = protein
                        organism = Citrobacter farmeri
SEQUENCE: 15
MKTLLSTTAL MLCAAISCAQ AAEKNDWHFN IGAMYEIENV EGYGEDMDGL AEPSVYFNAA    60
NGPWRISLAY YQEGPVDYSA GKRGTWFDRP ELEVHYQIQE SDEFSFGLTG GFRNYGYHYV   120
NEAGKDTANM QRWKVQPDWD VKITDDLRFS GWLSMYQFVN DLSTTGYADS RLESETGLHY   180
TFNETVGVIV NYYLERGFNL ADHRNNGEFS TQEIRAYLPL SLGNTTLTPY TRIGLDRWSN   240
WDWRDDPERE GHDFNRLGLQ YAYDFQNGLS MTLEYAYEWE DHDEGESDRF HYAGVGVNYA   300
F                                                                  301

SEQ ID NO: 16           moltype = AA  length = 31
FEATURE                 Location/Qualifiers
REGION                  1..31
                        note = Description of Artificial Sequence: Synthetic
```

```
                              polypeptide
source                        1..31
                              mol_type = protein
                              organism = synthetic construct
SEQUENCE: 16
EKEKEKGSHH HHHHGSGGAH IVMVDAYKPT K                                       31

SEQ ID NO: 17                 moltype = AA   length = 302
FEATURE                       Location/Qualifiers
REGION                        1..302
                              note = Description of Artificial Sequence: Synthetic
                               polypeptide
source                        1..302
                              mol_type = protein
                              organism = synthetic construct
SEQUENCE: 17
MDKFHYAGVG VNYSFGSGEE RNDWHFNIGA MYEIENVEGY GEDMDGLAEP SVYFNAANGP         60
WRIALAYKQE GPVDYSAGKR GTWFDRPELE VHYQFLENDD FSFGLTGGFR NYGYHYVDEP        120
GKDTANMQRW KIAPDWDVKL TDDLRFNGWL SMYKFANDLN TTGYADTRVE TETGLQYTFN        180
ETVALRVNYY LERGFNMDDS RNNGEFSTQE IRAYLPLTLG NHSVTPYTRI GLRAGHDFNR        240
VGLFYGYDFQ NGLSVSLEYA FEWQDHDEGD SEKEKEKGSH HHHHGSGGA HIVMVDAYKP         300
TK                                                                      302

SEQ ID NO: 18                 moltype = AA   length = 6
FEATURE                       Location/Qualifiers
REGION                        1..6
                              note = Description of Artificial Sequence: Synthetic 6xHis
                               tag
source                        1..6
                              mol_type = protein
                              organism = synthetic construct
SEQUENCE: 18
HHHHHH                                                                    6

SEQ ID NO: 19                 moltype = AA   length = 15
FEATURE                       Location/Qualifiers
REGION                        1..15
                              note = Description of Artificial Sequence: Synthetic peptide
source                        1..15
                              mol_type = protein
                              organism = synthetic construct
SEQUENCE: 19
GGGGSGGGGS GGGGS                                                         15

SEQ ID NO: 20                 moltype = AA   length = 8
FEATURE                       Location/Qualifiers
REGION                        1..8
                              note = Description of Artificial Sequence: Synthetic peptide
source                        1..8
                              mol_type = protein
                              organism = synthetic construct
SEQUENCE: 20
EKEKEKGS                                                                  8

SEQ ID NO: 21                 moltype = AA   length = 11
FEATURE                       Location/Qualifiers
REGION                        1..11
                              note = Description of Artificial Sequence: Synthetic peptide
source                        1..11
                              mol_type = protein
                              organism = synthetic construct
SEQUENCE: 21
HHHHHHGSGG K                                                             11

SEQ ID NO: 22                 moltype = AA   length = 13
FEATURE                       Location/Qualifiers
REGION                        1..13
                              note = Description of Artificial Sequence: Synthetic peptide
source                        1..13
                              mol_type = protein
                              organism = synthetic construct
SEQUENCE: 22
AHIVMVDAYK PTK                                                           13
```

```
SEQ ID NO: 23          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 23
RSKLG                                                                           5
```

We claim:

1. A method for sequencing a nucleic acid, the method comprising:
   (a) providing a nanopore comprising an OmpG variant, wherein the OmpG variant comprises an amino acid sequence that is at least 95% identical to an amino acid sequence of SEQ ID NO: 2 that has been modified to comprise (i) a deletion of one or more of loop-6 amino acids 216-227, (ii) an E229A amino acid substitution, and (iii) a D215 deletion, wherein the nanopore is disposed within a membrane that is adjacent or in proximity to a sensing electrode;
   (b) providing a plurality of tagged nucleotides into a reaction chamber comprising the nanopore, wherein each tagged nucleotide of the tagged nucleotides comprises a tag coupled to a nucleotide, the tag being detectable by the nanopore;
   (c) carrying out a polymerization reaction via a polymerase that is coupled to the OmpG variant, thereby incorporating a tagged nucleotide of the tagged nucleotides into a growing nucleotide strand, the growing nucleotide strand being complementary to a single stranded nucleic acid molecule from the nucleic acid sample; and
   (d) during the polymerization reaction, detecting, by the nanopore and with the sensing electrode, the tag coupled to the nucleotide that is incorporated into the growing nucleotide strand.

2. The method of claim 1, wherein the OmpG variant further comprises a mutation of one or more of amino acids R211, E15, R68, Y50, E152, E174, E17, Y259, K114, E174, F66, or E31 of SEQ ID NO:2.

3. The method of claim 2, wherein the mutation comprises one or more of a R211N, R68N, Y50K, Y50N, or E17K mutation of SEQ ID NO:2.

4. The method of claim 3, wherein the mutation of SEQ ID NO: 2 is a Y50K amino acid substitution.

5. The method of claim 1, wherein the OmpG variant further comprises a SpyTag construct.

6. The method of claim 1, wherein the OmpG variant comprises a deletion corresponding to each of amino acids 216-227 of SEQ ID NO: 2.

7. The method of claim 1, wherein the polymerase is coupled to the OmpG variant via the SpyTag construct.

8. The method of claim 1, wherein the OmpG variant nanopore reduces spontaneous gating of the nanopore as compared to a parental OmpG nanopore.

9. The method of claim 1, wherein the nanopore comprising the OmpG variant has a reduced ionic current noise as compared to a nanopore comprising a parental OmpG.

10. The method of claim 9, wherein the reduction is a reduction in downward current and upward current.

11. A method for sequencing a nucleic acid, the method comprising:
    (a) providing a nanopore comprising an OmpG variant, wherein the OmpG variant comprises an amino acid sequence that is at least 95% identical to an amino acid sequence of SEQ ID NO: 2 that has been modified to comprise (i) a deletion of one or more of loop-6 amino acids 216-227, (ii) an E229A amino acid substitution, and (iii) a Y50K substitution, wherein the nanopore is disposed within a membrane that is adjacent or in proximity to a sensing electrode;
    (b) providing a plurality of tagged nucleotides into a reaction chamber comprising the nanopore, wherein each tagged nucleotide of the tagged nucleotides comprises a tag coupled to a nucleotide, the tag being detectable by the nanopore;
    (c) carrying out a polymerization reaction via a polymerase that is coupled to the OmpG variant, thereby incorporating a tagged nucleotide of the tagged nucleotides into a growing nucleotide strand, the growing nucleotide strand being complementary to a single stranded nucleic acid molecule from the nucleic acid sample; and
    (d) during the polymerization reaction, detecting, by the nanopore and with the sensing electrode, the tag coupled to the nucleotide that is incorporated into the growing nucleotide strand.

12. The method of claim 11, wherein the OmpG variant further comprises a mutation of one or more of amino acids R211, E15, R68, E152, E174, E17, D215, Y259, K114, E174, F66, or E31 of SEQ ID NO: 2.

13. The method of claim 12, wherein the mutation comprises one or more of a R211N, R68N, E17K, or D215 mutation of SEQ ID NO:2.

14. The method of claim 12, wherein the mutation is a D215 deletion.

15. The method of claim 11, wherein the OmpG variant further comprises a SpyTag construct.

16. The method of claim 11, wherein the OmpG variant comprises a deletion corresponding to each of amino acids 216-227 of SEQ ID NO: 2.

17. The method of claim 11, wherein the polymerase is coupled to the OmpG variant via the SpyTag construct.

18. The method of claim 11, wherein the OmpG variant nanopore reduces spontaneous gating of the nanopore as compared to a parental OmpG nanopore.

19. The method of claim 11, wherein the nanopore comprising the OmpG variant has a reduced ionic current noise as compared to a nanopore comprising a parental OmpG.

20. The method of claim 19, wherein the reduction is a reduction in downward current and upward current.

* * * * *